(12) United States Patent
Brand

(10) Patent No.: US 12,121,709 B1
(45) Date of Patent: Oct. 22, 2024

(54) ADAPTABLE MULTIPROCEDURAL SHARPS SAFETY DEVICE

(71) Applicant: Christopher Brand, Muncie, IN (US)

(72) Inventor: Christopher Brand, Muncie, IN (US)

(*) Notice: Subject to any disclaimer, the term of this patent is extended or adjusted under 35 U.S.C. 154(b) by 0 days.

(21) Appl. No.: 16/826,242

(22) Filed: Mar. 22, 2020

Related U.S. Application Data

(60) Provisional application No. 62/822,287, filed on Mar. 22, 2019.

(51) Int. Cl.
*A61M 5/32* (2006.01)

(52) U.S. Cl.
CPC ... *A61M 5/3257* (2013.01); *A61M 2005/3258* (2013.01); *A61M 5/3275* (2013.01)

(58) Field of Classification Search
CPC ........ A61M 5/3257; A61M 2005/3258; A61M 5/3275; A61M 5/326; A61M 5/3243; A61M 2005/3246; A61M 2005/3261; A61M 2005/3212; A61M 25/0612; A61M 2025/026; A61M 5/50; A61M 5/3213; A61M 5/321; A61M 2005/3217; A61M 2005/3254; A61B 50/3001
USPC .......................................................... 604/198
See application file for complete search history.

(56) References Cited

U.S. PATENT DOCUMENTS

| | | |
|---|---|---|
| 1,268,996 A | 12/1882 | Brinkerhoff |
| 2,367,703 A | 1/1945 | Vaughan |
| 3,052,241 A | 9/1962 | Myerson et al. |
| 3,063,450 A | 11/1962 | Myerson et al. |
| 3,434,473 A | 3/1969 | Smith |
| 3,853,010 A | 12/1974 | Christen et al. |
| 4,631,057 A | 12/1986 | Mitchell |
| 4,693,708 A | 9/1987 | Wanderer et al. |
| 4,723,943 A | 2/1988 | Spencer |
| 4,799,927 A | 1/1989 | Davis et al. |
| 4,840,185 A | 6/1989 | Hernandez |
| 4,867,172 A * | 9/1989 | Haber ................. A61M 5/3129 600/576 |
| 4,908,023 A | 3/1990 | Yuen |
| 4,921,489 A * | 5/1990 | Frizzell ............... A61M 5/3202 604/263 |
| 4,923,445 A | 5/1990 | Ryan |
| 4,935,013 A * | 6/1990 | Haber ................. A61M 5/3275 604/192 |
| 4,955,871 A * | 9/1990 | Thomas .................. A61M 5/50 222/215 |
| 4,973,315 A | 11/1990 | Sincock |
| 4,986,817 A | 1/1991 | Code |
| 4,998,920 A | 3/1991 | Johnson |
| 5,021,047 A | 6/1991 | Movern |
| 5,041,099 A | 8/1991 | Gelabert |
| 5,078,695 A | 1/1992 | Farrar et al. |
| 5,085,647 A | 2/1992 | Henderson et al. |
| 5,092,462 A | 3/1992 | Sagstetter et al. |
| 5,209,738 A | 5/1993 | Bruno |
| 5,259,840 A | 11/1993 | Boris |

(Continued)

FOREIGN PATENT DOCUMENTS

| | | |
|---|---|---|
| GB | 2198644 | 6/1988 |
| WO | 2005041846 | 5/2005 |

*Primary Examiner* — Michael J Tsai
*Assistant Examiner* — Nidah Hussain
(74) *Attorney, Agent, or Firm* — ICE MILLER LLP

(57) ABSTRACT

A medical sharps safety device that is affixable to a conventional medical syringe or other sharp device.

19 Claims, 15 Drawing Sheets

SAFETY DEVICE SHOWN DETACHED FROM ITS PRE-FILLED ORPHAN PAC AND CONNECTED TO A SYRING BARREL WHICH IS PRE-MANUFACTURED WITH THREADING FOR A LUER TIP

1. SYRINGE BARREL WITH THREADING FOR A LUER TIP
2. INTERLOCKING TEETH
3. FLEXIBLE SHARPS CONTAINMENT CHAMBER
4. FLEXIBLE PLASTIC
5. FLANGE THAT THE NEEDLE PASSES THROUGH
6. INJECTION NEEDLE
7. LEAF SPRINGS
8. SYRINGE BARREL

SAFETY DEVICE SHOWN IN THE OPEN PRE-INJECTION POSITION WITHOUT SAFETY DEVICE ACTIVATED

(56) References Cited

U.S. PATENT DOCUMENTS

| | | | |
|---|---|---|---|
| 5,295,972 A * | 3/1994 | Mischenko | A61M 5/3275 604/263 |
| 5,334,151 A | 8/1994 | Santilli | |
| 5,347,078 A | 9/1994 | Eckels | |
| 5,348,544 A * | 9/1994 | Sweeney | A61M 5/3275 128/919 |
| 5,395,338 A | 3/1995 | Gaba | |
| 5,403,288 A | 4/1995 | Stanners | |
| 5,405,330 A * | 4/1995 | Zunitch | A61M 5/34 604/272 |
| 5,509,907 A * | 4/1996 | Bevilacqua | A61M 5/3216 604/263 |
| 5,519,931 A | 5/1996 | Reich | |
| 5,582,594 A | 12/1996 | Chen | |
| 5,593,391 A | 1/1997 | Stanners | |
| 5,697,908 A | 12/1997 | Imbert et al. | |
| 5,718,689 A | 2/1998 | Stevenson | |
| 5,725,503 A | 3/1998 | Arnett | |
| 5,941,857 A | 8/1999 | Nguyen et al. | |
| 6,036,675 A | 3/2000 | Thorne et al. | |
| 6,287,282 B1 | 9/2001 | Bonaldo et al. | |
| 6,409,706 B1 * | 6/2002 | Loy | A61M 5/3275 604/110 |
| 6,585,702 B1 | 7/2003 | Brunel | |
| 6,986,759 B1 * | 1/2006 | Jeremijevic | A61M 5/3275 604/110 |
| 7,361,159 B2 * | 4/2008 | Fiser | A61M 5/3275 604/192 |
| 8,603,039 B2 | 12/2013 | Brand | |
| 2002/0193748 A1 * | 12/2002 | Cocker | A61M 5/326 604/198 |
| 2003/0004465 A1 * | 1/2003 | Ferguson | A61B 5/15003 604/198 |
| 2004/0010227 A1 | 1/2004 | Riesenberger et al. | |
| 2010/0114036 A1 * | 5/2010 | Steyn | A61M 5/3275 604/198 |

* cited by examiner

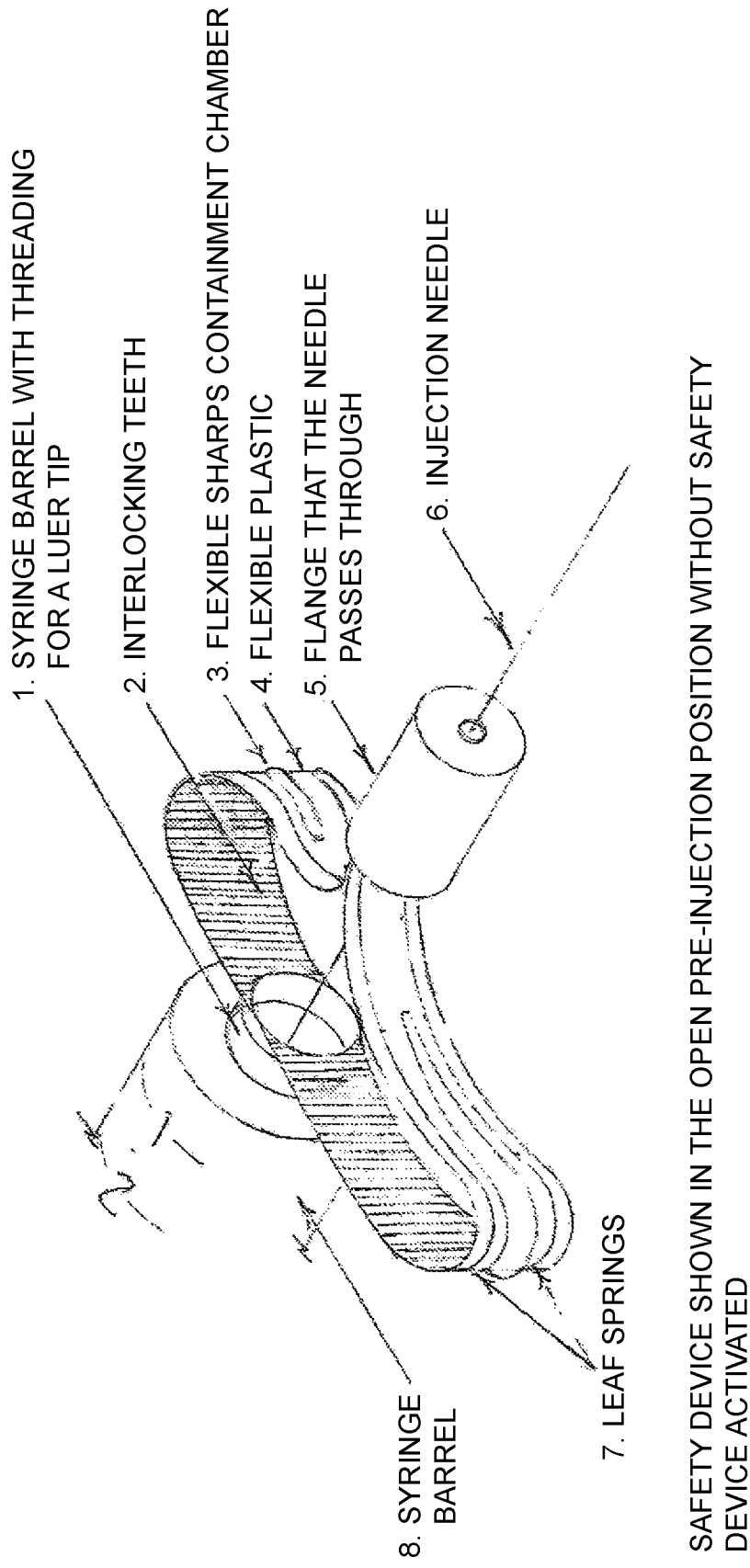

FIGURE 1
SAFETY DEVICE SHOWN DETACHED FROM ITS PRE-FILLED ORPHAN PAC AND CONNECTED TO A SYRINGE BARREL WHICH IS PRE-MANUFACTURED WITH THREADING FOR A LUER TIP

1. SYRINGE BARREL WITH THREADING FOR A LUER TIP
2. INTERLOCKING TEETH
3. FLEXIBLE SHARPS CONTAINMENT CHAMBER
4. FLEXIBLE PLASTIC
5. FLANGE THAT THE NEEDLE PASSES THROUGH
6. INJECTION NEEDLE
7. LEAF SPRINGS
8. SYRINGE BARREL

SAFETY DEVICE SHOWN IN THE OPEN PRE-INJECTION POSITION WITHOUT SAFETY DEVICE ACTIVATED

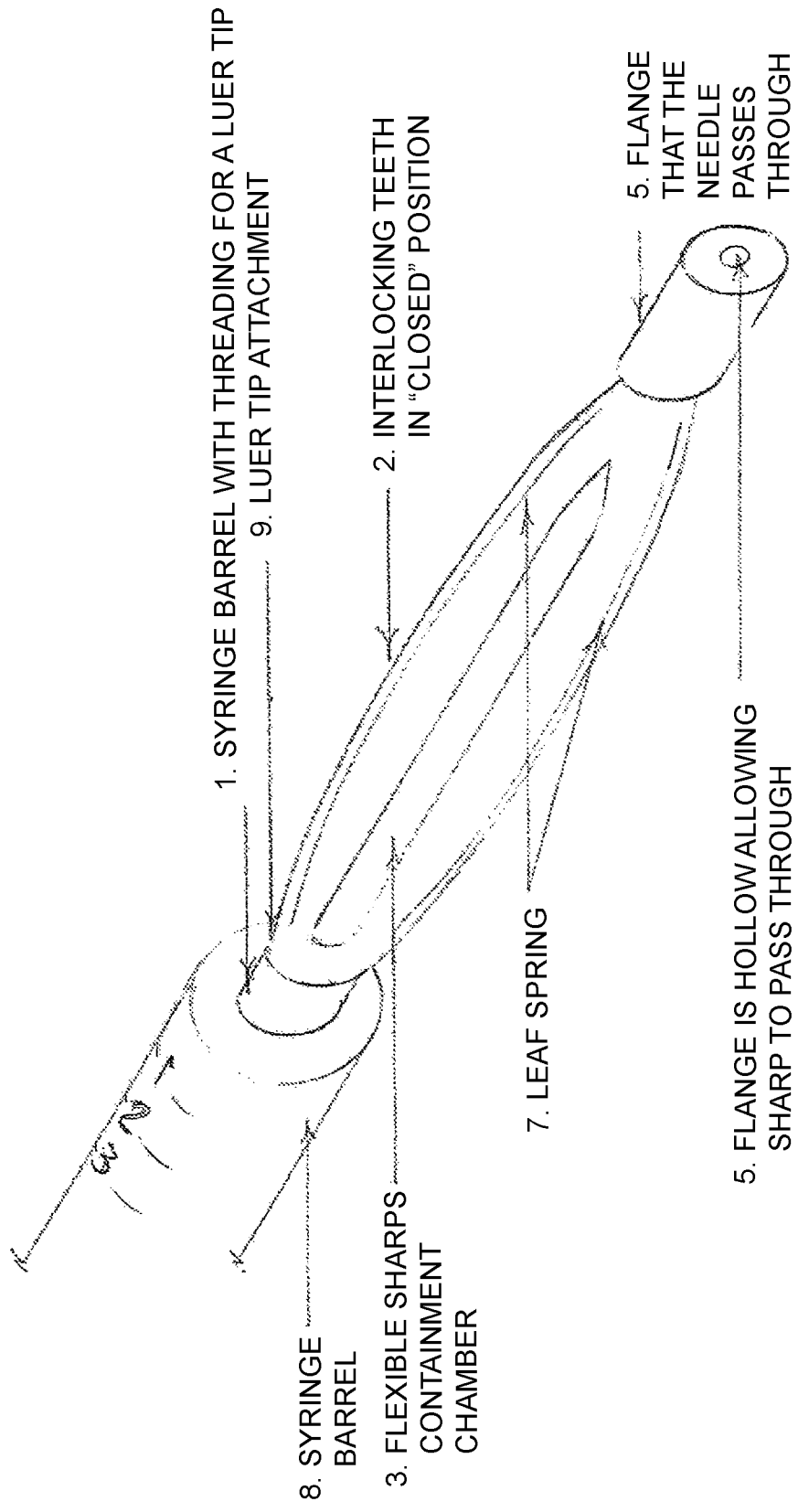

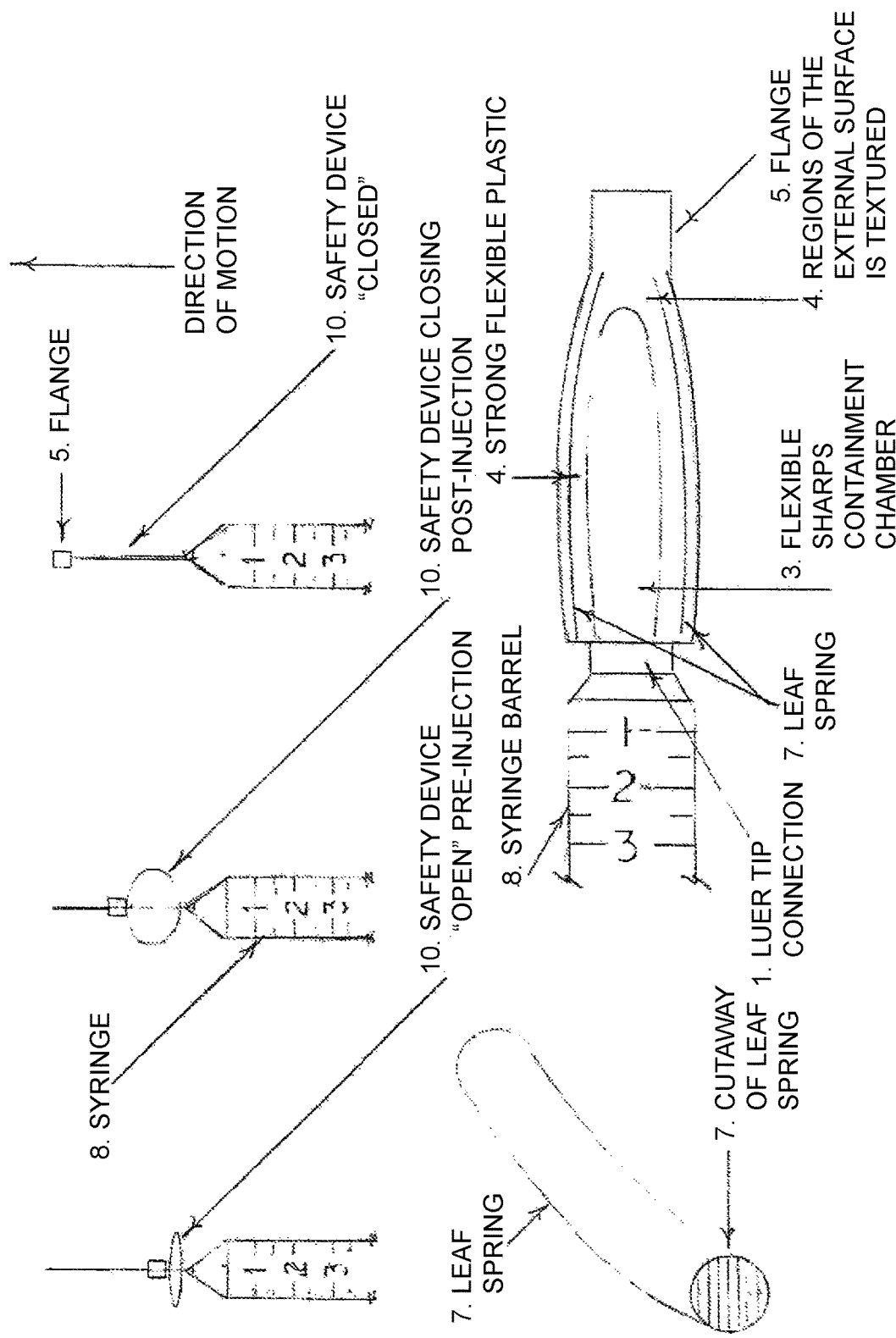

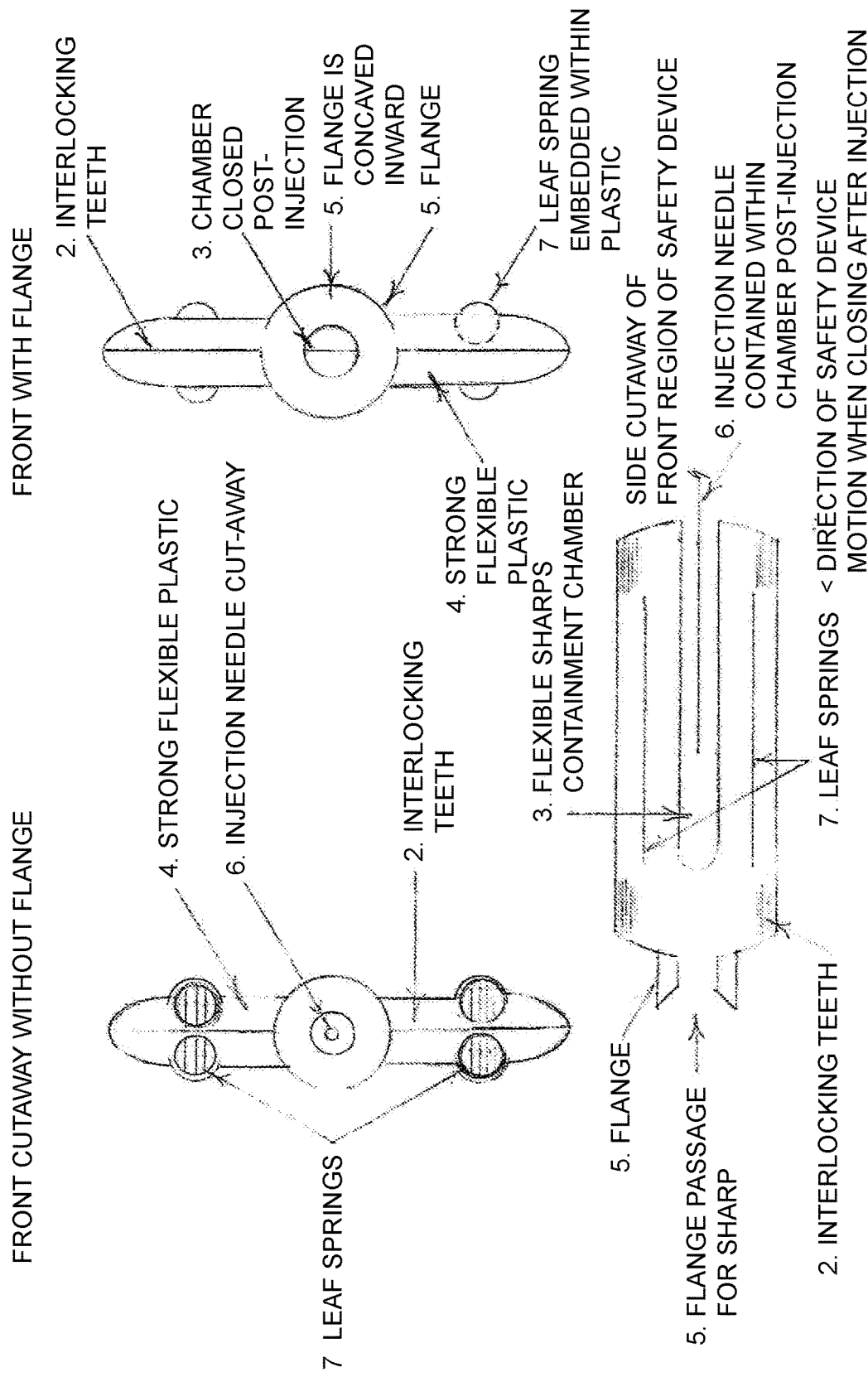

FIGURE 5.
SAFETY DEVICE REAR PERSPECTIVE
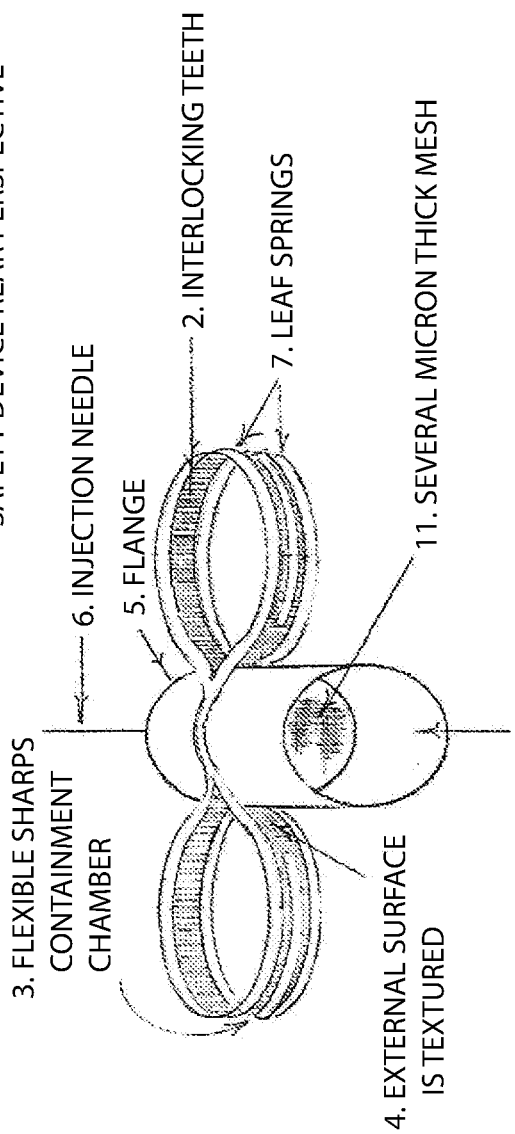
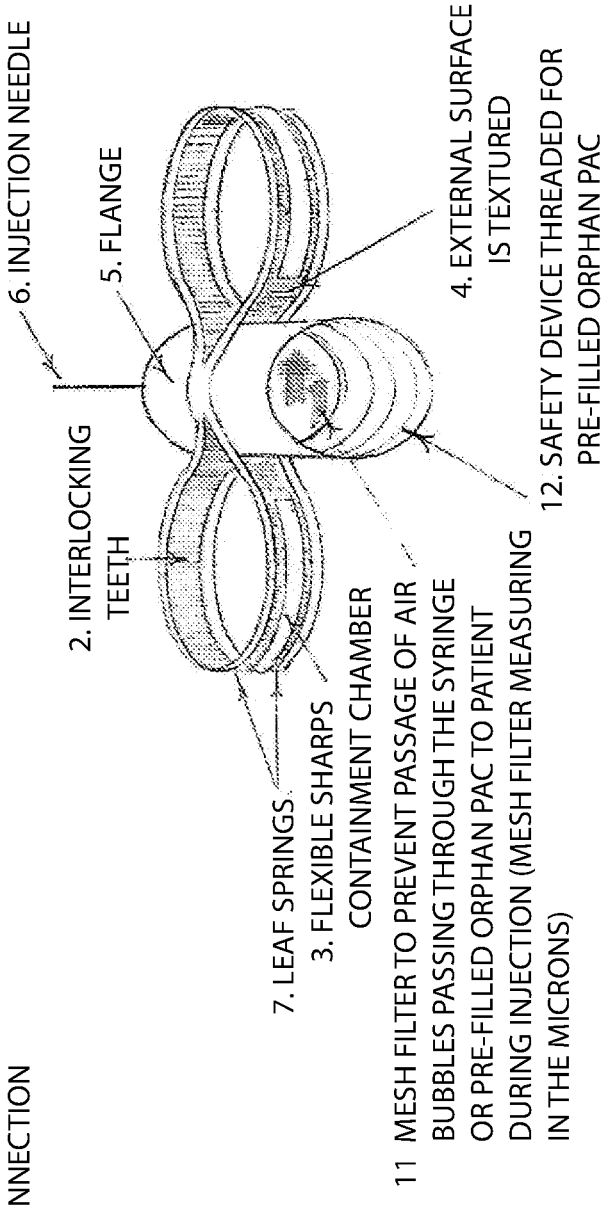

BALL AND SOCKET JOINT CONNECTION BETWEEN SAFETY DEVICE AND THE OPTIONAL PRE-FILLED ORPHAN PAC

REAR EXTERNAL VIEW OF THE PRE-FILLED ORPHAN PAC

TOP VIEW OF SAFETY DEVICE WITH PRE-FILLED ORPHAN PAC ATTACHED

AERIAL VIEW OF COMPLETE SAFETY DEVICE AND ORPHAN PAC WITH PRE-USE NEEDLE CAP

SCALPEL WITH THE "ADAPTABLE MULTI-PROCEDURAL SHARP SAFETY DEVICE" IN THE OPEN PRE-USE POSITION

SCALPEL WITH THE "ADAPTABLE MULTI-PROCEDURAL SHARPS SAFETY DEVICE" IN THE CLOSED POST-USE POSITION

SCALPEL INTERNAL VIEW WITH ADAPTABLE MULTI-PROCEDURAL SHARPS SAFETY DEVICE IN THE CLOSED POST-USE POSITION

ADDITIONAL RENDERING OF THE "ADAPATABLE MULTI - PROCEDURAL SHARPS SAFETY DEVICE" WITHOUT PRE-FILLED ORPHAN PAC VISIBLE

ADAPTABLE MULTIPROCEDURAL SHARPS SAFETY DEVICE

BACKGROUND

Syringes are medical devices used to inject fluids into a body and/or withdraw fluids from within a body or its cavities. Conventional medical syringes typically include a barrel portion with one end configured to mate with a conventional piercing element, such as a pointed hollow needle or cannula. A plunger rod is inserted through the opposing end of the barrel portion. By engaging the plunger rod with an elastomeric stopper element fitted in a fluid-tight manner within the interior of the barrel, a user can apply manual force to the plunger to either withdraw or deliver the syringe contents.

During use, it is not uncommon for the needle portions to be involved in accidental needle sticks or punctures. Such puncture incidents can pose a great health risk to medical personnel via the accidental transmission of pathogens and/or pharmacological substances. Thus, it is of utmost importance to provide protection for medical personnel from pathogen-contaminated blood, body fluids, and/or pharmacological substances still present in or on the syringe needle.

Previous safety devices have failed to meet these criteria. There is a need for a safety device which is easily and permanently affixed to a conventional medical syringe or other sharp device without special tools, especially during times of high stress and relative inattention such as during emergencies. There also exists a need for a safety device that is comprised of a minimal number of parts which are easily formed using mass production techniques. Various aspects of the present disclosure address these needs.

BRIEF DESCRIPTION OF THE DRAWINGS

The features and advantages of this disclosure, and the manner of attaining them, will be more apparent and better understood by reference to the following descriptions of the disclosed methods and systems, taken in conjunction with the accompanying drawings, wherein:

FIG. 1 shows a perspective view of a sharps safety device according to at least one embodiment of the present disclosure;

FIG. 2 shows a perspective view of a sharps safety device according to at least one embodiment of the present disclosure;

FIG. 3 shows features of a sharps safety device according to at least one embodiment of the present disclosure;

FIG. 4 shows features of a sharps safety device according to at least one embodiment of the present disclosure;

FIG. 5 shows a perspective view of a sharps safety device according to at least one embodiment of the present disclosure;

DESCRIPTION

Figure 6:
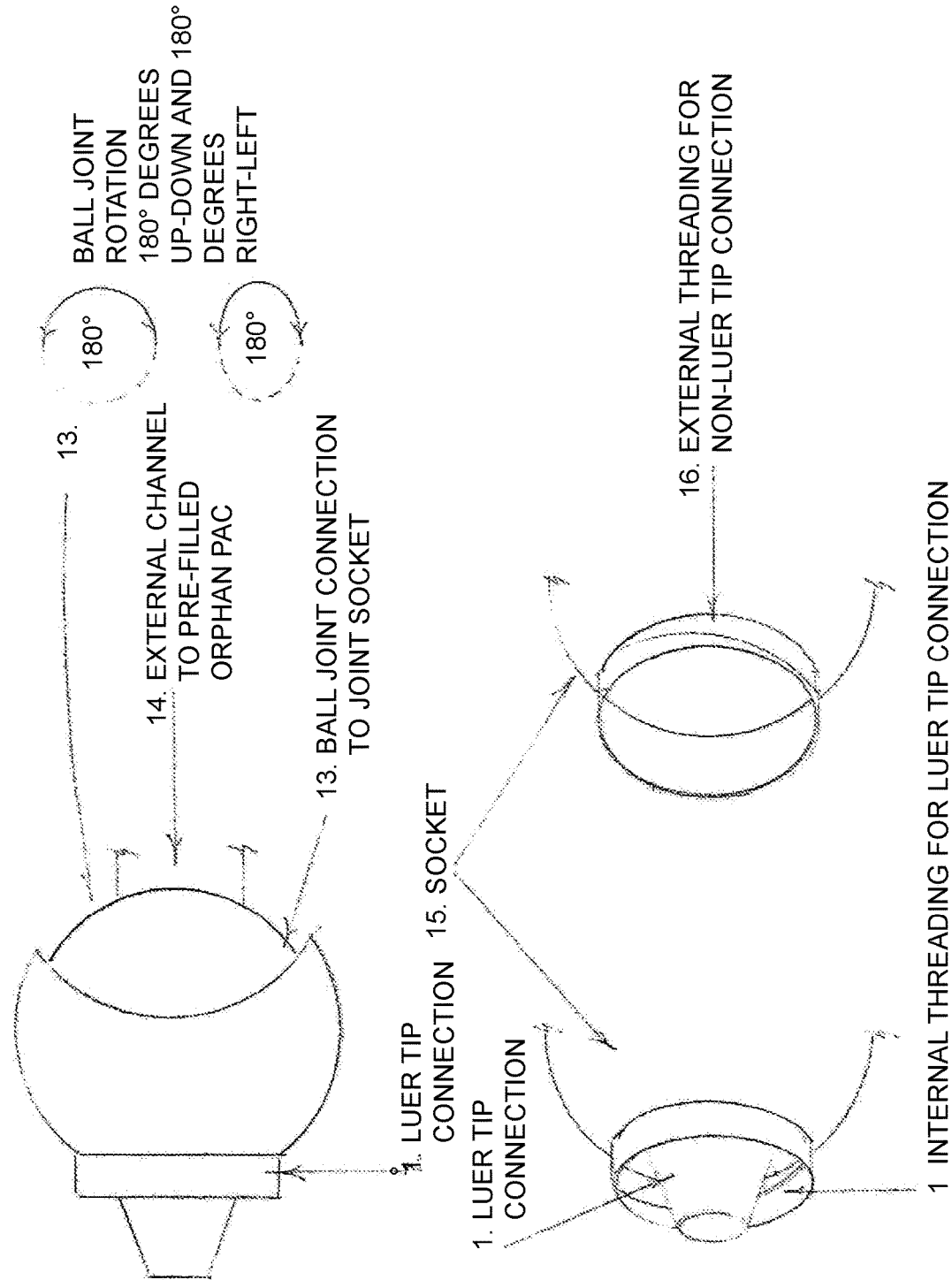
FIG. 6 shows features of a sharps safety device according to at least one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Explanatory Notes for FIG. 1

Safety Device Shown Detached from the Pre-Filled Orphan Pac and Connected to a Syringe Barrel which is Pre-manufactured with Threading for a Luer Tip The notes and discussions on this page refer to the drawing labeled, "FIG. 1". "FIG. 1" is numbered 1 thru 8. Numbers are placed throughout the illustration and are associated with corresponding arrows pointing to various sections and aspects of the drawing which need further explanation. This methodology allows for a clear and concise explanation of the various sections and sub-sections of the mechanism.

Description of FIG. 1

Figure 9:
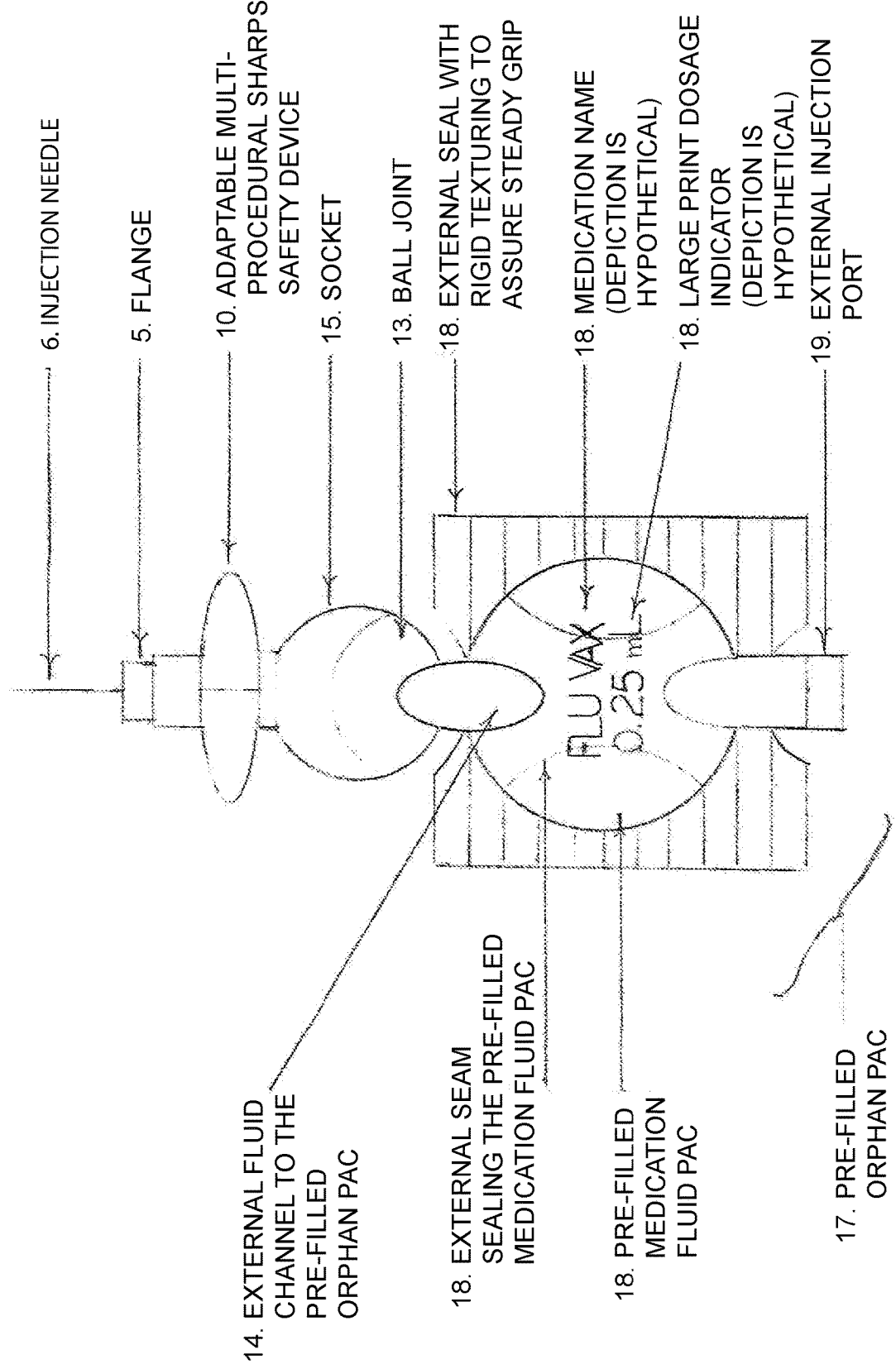
FIG. 9 shows a top view of a sharps safety device according to at least one embodiment of the present disclosure.
Figure 10:
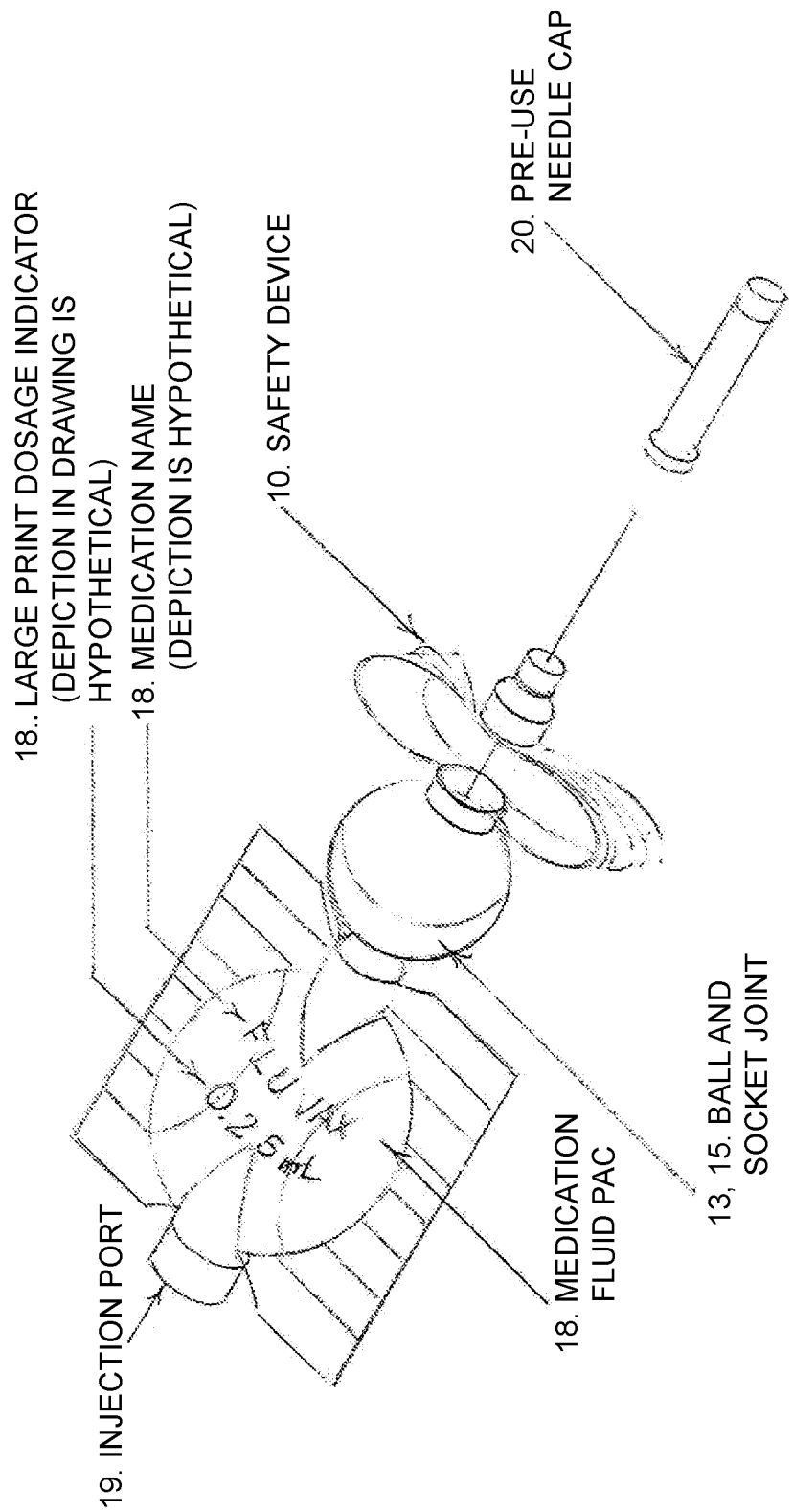
FIG. 10 shows features of a sharps safety device according to at least one embodiment of the present disclosure.

The "Adaptable Multi-Procedural Sharps Safety Device with Optional Orphan Pac" as seen in "FIGS. 9 and 10" is a primary and a specialized care device. The following document will examine its capabilities in greater detail. In the diagram labeled, "FIG. 1" the "Adaptable Multi-Procedural Sharps Safety Device" has been manually attached to a "Syringe Barrel with Threading for a Luer Tip" (1). Once the safety device is threaded onto a "Syringe Barrel" (8), or "Pre-Filled Orphan Pac" "FIG. 9" (17) [which appears in later "Explanatory Notes"] a rib located near the threads will act as a block or brake preventing the safety device from ever being unthreaded. The safety device and needle assembly may also be manufactured as a unit permanently attached to a "Syringe Barrel" (8) which would come in a wide range of sizes or attached to the "Pre-Filled Orphan Pac" "FIG. 9" (17). As will be explained in greater detail further into this document, the "Pre-Filled Orphan Pac" "FIG. 9" (17) is an injection delivery device specifically designed for "Adaptable Multi-Procedural Sharps Safety Device" and will be pre-filled with any given medication. The user can opt to use this as their preferred injection delivery method or attach the safety device and needle to a "Syringe Barrel" (8) of their choice, using a "Luer Tip or Luer Slip Tip Connection". The "Adaptable Multi-Procedural Sharps Safety Device" illustrated in "FIG. 1" is attached to a "Syringe Barrel" (8) rather than the optional "Pre-Filled Orphan Pac" as seen in "FIG. 9" (17). "FIG. 1" is shown in the "Open Position," meaning the "Adaptable Multi-Procedural Sharps Safety Device", "Flexible Plastic"

(4), "Leaf Springs" (7) on either side of the device, and "Flange that the Needle Passes Through" (5) are all "flexed" into position fully exposing the "Syringe Needle" (6). At this point the user is able to load and perform injections or other medical procedures, withdrawal blood for phlebotomy work, or give an injection with a "Pre-Filled Orphan Pac" "FIG. 9" (17). Activation automatically occurs once the "Syringe Needle" (6) is withdrawn from the patient and the safety device moves into the "closed" and "active" position. At this stage, the "Leaf Springs" (7) which are located on either side of the "Adaptable Multi-Procedural Sharps Safety Device" which are made of either a "Shape Memory Alloy" or other material containing the characteristics of shape memory, return to their previously "un-flexed" state assuming a more linear position. Simultaneously, the two sections of the "Flexible Sharps Containment Chamber" (3) move in a forward direction eventually snapping and locking into position. This motion quickly and permanently encases the "Syringe Needle" (6) into a puncture and leak proof and air-tight chamber. As an added layer of stability, the "Adaptable Multi-Procedural Sharps Safety Device's" "Interlocking Teeth" (2), located on the interior wall the mechanism, interlock with each other permanently snapping closed; thus, preventing the two sides from coming apart. The pattern of the "Interlocking Teeth" (2) will vary depending on the size, type, and shape of sharp being contained. The purpose of the "Flange" (5) is to provide a safe passage for the "Injection Needle" (6) or as will be discussed later "Scalpel Blade" "FIG. 11" (21) to travel through without Interfering with the "Adaptable Multi-Procedural Sharps Safety Device's" function or the medical procedure. Additionally, the "Flange" (5) provides another important function; structural integrity. Once the device is activated and moves into the "closed" position a bio-hazard warning symbol will be prominently displayed indicating that the unit is medical waste but is safely secured and ready to be disposed of appropriately.

Another format of the "Adaptable Multi-Procedural Sharps Safety Device" as visible in "FIG. 5" will be that the safety device will also be available in luminous plastics. The "Injection Needle" (6) will have the ability to be coated in a biologically safe, medically approved luminous material. This will be especially useful to the individual administering the injection in low-light environments such as emergency care or triage situations.

Explanation of FIG. 1 Illustration Numbers and their Corresponding Arrows

1. Syringe Barrel with Threading for Luer Tip

The "Syringe Barrel with Threading for a Luer Tip" (1) is a widely used format of "Syringe Barrel" (8) on the market today. For this reason, the "Adaptable Multi-Procedural Sharps Safety Device" presented in "FIG. 1" is a highly adaptable device that will also be capable of being attached to a "Syringe Barrel" (8) using a "Luer Tip or Luer Slip Tip Connection". As previously noted, the "Adaptable Multi-Procedural Sharps Safety Device" may also be manufactured permanently attached to a "Syringe Barrel" (8) of various sizes, or permanently or manually attach to a "Pre-Filled Orphan Pac" "FIG. 9" (17).

Note: For information on the "Pre-Filled Orphan Pac" see "Explanatory Notes" for: "FIG. 7" (17).

2. "Interlocking Teeth"

The "Interlocking Teeth" (2) are an integral component of the "Adaptable Multi-Procedural Sharps Safety Device" because they assist in locking the device in place once "activated." The "Leaf Springs" (7) present on either side of the safety device are embedded within the "Flexible Plastic" (4), along with the "Flexible Sharps Containment Chamber" (3) which automatically move forward into the "closed" or "active" position once the medical procedure is complete. Once activated, the "Interlocking Teeth" (2) lock in place and snap shut. The pattern which appears on the underside of the "Interlocking Teeth" (2) will vary based upon the size and shape of the sharp being contained. Additional clamps or clasps will be in strategic locations throughout the "Flexible Plastic" (4) to assist in permanently locking the device shut and "closed" after use. Once the "Interlocking Teeth" (2) are in the "closed" and "active" position both sides of the "Flexible Sharps Containment Chamber" (3) will be permanently locked in place. The chamber when in the "closed" position permanently encases the needle or sharp in a puncture proof and leakproof enclosure which will prevent it from leaking potential hazardous waste, causing a sharps injury, or from being re-used in another procedure.

3. Flexible Sharps Containment Chamber

The "Flexible Sharps Containment Chamber" (3) is a critical part of the "Adaptable Multi-Procedural Sharps Safety Device" because it permanently encloses the "Injection Needle" (6) or "Scalpel Blades" "FIG. 11" (21) as will be examined later. Above and below the chamber on either side of the "Adaptable Multi-Procedural Sharps Safety Device" are "Leaf Springs" (7). On the underside of the "Flexible Plastic" (4) are the "Interlocking Teeth" (2). Once the two sides of the "Flexible Sharps Containment Chamber" (3) become "active" the "Injection Needle" (6), or as previously mentioned, the "Scalpel Blade" FIG. 11" (21) will be permanently sealed within the "Adaptable Multi-Procedural Sharps Safety Device". Like the "Leaf Springs" (7) the "Flexible Sharps Containment Chamber" (3) will be made of a flexible memory-based material such as a "Shape Memory Alloy" or other material with shape memory characteristics which will allow it to flex and unflex without cracking or breaking during the enclosure procedure. The chamber construction will be highly flexible yet impenetrable once in the "closed" position preventing any portion of the sharp or "Injection Needle" (6) in this case from puncturing through the chamber while simultaneously containing all remaining fluids that may exist on the sharp within the chamber. This is vital since blood-borne pathogens may be present on any sharp after use. Once the "Adaptable Multi-Procedural Sharps Safety Device" is "activated" no further injections including blood removal or other medical procedures will be possible because the safety device will automatically disable the unit. As visible in "FIG. 1" the "Flexible Sharps Containment Chamber" (3) is connected to the "Flange" (5) on one end and is also embedded within the "Flexible Plastic (4). The "Flange" (5) as will be detailed, provides overall stability to the device as well as strength and flexibility for seamless function before, during, and after an injection, bloodwork, or other medical procedure.

Note: For further information on the "Scalpel Blade" see "Explanatory Notes" for: "FIG. 11" (21).

4. Flexible Plastic

The "Flexible Plastic" (4) of which the "Adaptable Multi-Procedural Sharps Safety Device" is composed will hold an integral purpose to the overall construction of the "Adaptable Multi-Procedural Sharps Safety Device" because so many components of the safety device are either embedded within the plastic or attached to the plastic. The "Flexible Plastic" (4) contains three vital regions of the "Adaptable Multi-Procedural Sharps Safety Device" which are the "Leaf Springs" (7), the "Flexible Sharps Containment Chamber"

(3), and the "Interlocking Teeth" (2) located on the underside of the safety device. As explained, the "Flexible Plastic" (4) provides overall stability to the "Adaptable Multi-Procedural Sharps Safety Device" as well as strength and flexibility for seamless function before, during, and after an injection, bloodwork, or other medical procedure takes place. It helps to control the speed of closure of the device when "activated" to assist in preventing malfunction or injury while assuring instantaneous enclosure of the sharp.

5. Flange that the Sharp Passes Through

The "Flange" (5) provides two vital functions for the "Adaptable Multi-Procedural Sharps Safety Device". First, it provides a safe passage for the sharp, or in this case the "Injection Needle" (6) to pass through as the device "open's" and "closes" free of interference or obstruction of the sharp which could potentially cause injury to the individual receiving the medical procedure. Second, the "Flange" (5) is the central point where numerous components such as the "Leaf spring" (7), "Flexible Sharps Containment Chamber" (3), and "Interlocking Teeth" (2) are interconnected and ultimately attached to the "Flange" (5). This enables the "Adaptable Multi-Procedural Sharps Safety Device" to maintain overall stability and strength while also allowing the device to "flex opened" or "unflex closed" without misaligning or malfunctioning. Additionally, the external entry into the "Flange" (5) can be enlarged enough to allow a standard "Luer Tip or Luer Slip Tip Needle" to pass through the "Flange" (5) and be threaded internally utilizing "Luer Threading". This is yet another demonstration of the adaptability of the "Adaptable Multi-Procedural Sharps Safety Device". The opening, shape, and diameter of the "Flange" (5) will vary based upon the type of sharp to be contained within the safety device.

Note: For further information on the "Scalpel Blade" see "Explanatory Notes" for: "FIG. 11" (21).

6. Injection Needle

The "Injection Needle" (6) will come in multiple formats within the "Adaptable Multi-Procedural Sharps Safety Device". First, an "Injection Needle" (6) of any length and gauge may be permanently factory attached and safely embedded within the "Adaptable Multi-Procedural Sharps Safety Device". In this instance, "Adaptable Multi-Procedural Sharps Safety Device" would itself also be factory attached to a "Syringe Barrel" (8) or a "Pre-Filled Orphan Pac" "FIG. 9" (17).

A Second method of attachment of the "Adaptable Multi-Procedural Sharps Safety Device" would be a safety device pre-manufactured without a sharp pre-installed, in this case, an "Injection Needle" (6). In this case, the unit would have internal threading to accommodate a "Luer Tip or Luer Slip Tip Connection" and "Flange" (5) enlarged enough to allow an independent "Luer Tip Needle" of any size and gauge to be inserted through the opening of the "Flange" (5) and attached to the "Adaptable Multi-Procedural Sharps Safety Device" via the internal threading. The "Adaptable Multi-Procedural Sharps Safety Device" would then be able to be manually threaded onto a "Syringe Barrel with Threading for a Luer Tip" (1) connection or a "Pre-Filled Orphan Pac" as seen in "FIG. 9" (17). In this case, the individual administering the medical procedure would have to select the size and gauge of "Luer Tip or Luer Slip Tip Needle" they wished to use as well as select the appropriate "Syringe Barrel" (8) or "Pre-Filled Orphan Pac" "FIG. 9"-(17).

A third format that the "Adaptable Multi-Procedural Sharps Safety Device" will have is an "Injection Needle" (6) of any length and gauge desired, or as will be detailed later a "Scalpel Blade" as seen in "FIG. 11" (21) permanently embedded and internally attached to the device. The individual administering the medical procedure would then select the appropriate size of "Syringe Barrel" (8), "Pre-Filled Orphan Pac" "FIG. 9" (17) or "Scalpel Blade" "FIG. 11" (21) that they wish to use and manually attach it to the correct receptacle. This method will allow greater variation and selection for the medical professional, and as mentioned previously, once the device is attached to a given receptacle like a "Syringe Barrel" (8), or a "Pre-Filled Orphan Pac" as seen in "FIG. 9" (17) or "Scalpel Blade" as seen in "FIG. 11" (21) it can never be removed.

Another feature that the "Adaptable Multi-Procedural Sharps Safety Device" will have is "Injection Needles" (6) made of medically approved bio-degradable sterile materials. The integration of bio-degradable needles will eliminate one of the most dangerous components of a drug delivery device which is the "Injection Needle" (6). The biodegrading of the needle over a given time will significantly reduce the risk of injury associated with the sharps after use.

Each "Adaptable Multi-Procedural Sharps Safety Device" will be prominently color coded allowing the individual performing the medical procedure or medical facility to easily select the appropriate "Adaptable Multi-Procedural Sharps Safety Device" for their purposes and intended use. Units will also contain Braille identification and instructions as well.

Note: For further information on the "Pre-Filled Orphan Pac" see "Explanatory Notes" for: "FIG. 7" (17).

See also: For further information on the "Scalpel Blade" see "Explanatory Notes" for: "FIG. 11" (21).

7. Leaf Springs

The "Leaf springs" (7) are located on either side of the "Adaptable Multi-Procedural Sharps Safety Device" and are composed of a form of "Shape Memory Alloy" or other highly flexible material which has shape memory capability and can revert to its original state once stress is no longer being applied to the spring. The depiction shown in "FIG. 1" shows the leaf springs in the "open" pre-injection position in which the springs are tightly "flexed" into the "open" position. After injection or medical procedure is complete the "Adaptable Multi-Procedural Sharps Safety Device" will automatically activate relieving pressure from the springs causing the "Leaf Springs" (7) and "Adaptable Multi-Procedural Sharps Safety Device" to move into the "closed" and "unflexed" position. One end of the "Leaf Springs" (7) are attached to the "Flange" (5) and depend upon it for structural integrity as well as strength and agility while the other end of the springs are attached to the safety device base.

Note: For further information on the "Leaf Spring" see "Explanatory Notes" for: "FIG. 1" (7) "FIG. 3" (7).

8. Syringe Barrel

As previously mentioned, the "Adaptable Multi-Procedural Sharps Safety Device" will also have the ability to attach to a "Syringe Barrel with a Luer Tip Connection" (1). Once the safety device is threaded onto a "Syringe Barrel" (8) or "Pre-Filled Orphan Pac" "FIG. 9" (17) a rib built into the plastic will act as a brake effectively preventing the "Adaptable Multi-Procedural Sharps Safety Device" from being unthreaded and removed from the "Syringe Barrel" (8). The same built-in rib brake will prevent the "Pre-Filled Orphan Pac" "FIG. 9" (17) from being unthreaded from the safety device once it is attached. This method will eliminate the problem of syringe re-use. The same brake will also be built into the plastic with the "Adaptable Multi-Procedural Sharps Safety Device" containing a "Scalpel Blade" "FIG. 11" (21) which will be examined later in this document. The application of this brake will assist in making all associated devices strictly limited to only medical procedure before being disposed of.

Note: For further information on the "Pre-Filled Orphan Pac" see "Explanatory Notes" for: "FIG. 7" (17).

Explanatory Notes for FIG. 2

Safety Device Shown Detached from its Pre-Orphan Pac and Connected to a Syringe Barrel which is Pre-manufactured with Threading for a Luer Tip The notes and discussions on this page refer to the drawing labeled, "FIG. 2". "FIG. 2" is numbered 1, 2, 3, 5, 7, 8, and 9. The numbers are placed throughout the illustration. They are associated with corresponding arrows which point to various sections and aspects of the drawing which need further explanation. This methodology allows for a clear and easy explanation of the various sections and sub-sections of the mechanism.

Description of FIG. 2

In the illustration shown in "FIG. 2", the "Adaptable Multi-Procedural Sharps Safety Device" is shown attached to a "Syringe Barrel with Threading for a Luer Tip" (1) and is in the "closed" post-injection position. The "Adaptable Multi-Procedural Sharps Safety Device" is "activated" and has permanently enclosed the "Injection Needle" "FIG. 1" (6). The "Interlocking Teeth are in the Closed Position" (2) and have locked in place. Both sides of the "Flexible Sharps Containment Chamber" (3) are tightly sealed preventing the sharp, or "Injection Needle" FIG. 1" (6) in this case, from penetrating the device wall while simultaneously sealing any remaining potentially bio-hazardous contents of the sharp safely inside the chamber. The "Leaf Spring[s]" (7) which appear on either side of the safety device have also returned to their naturally "unflexed" state and are assisting in keeping the "Adaptable Multi-Procedural Sharps Safety Device" tightly secured. The "Flange that the Sharp Passes Through" (5) is internally locked, and both sides of the "Flexible Sharps Containment Chamber" (3) are tightly pressed together forming an impenetrable cavity which effectively seals off the interior passage of the "Flange" (5). No matter what method of attachment the individual administering the medical procedure selects, whether it be a "Adaptable Multi-Procedural Sharps Safety Device" connected to a "Syringe Barrel with Threading for a Luer Tip" (1), a "Adaptable Multi-Procedural Sharps Safety Device" with the "Syringe Barrel" (8) and "Injection Needle" "FIG. 1" (6) permanently fused together, or a "Adaptable Multi-Procedural Sharps Safety Device" with a "Pre-Filled Orphan Pac" "FIG. 9" (17), the "Adaptable Multi-Procedural Sharps Safety Device" will operate the same. Once the unit is "activated" the device is permanently "disabled" and secured. The same holds true for "Adaptable Multi-Procedural Sharps" Safety Device" enclosing other sharps such as "Scalpel Blades" "FIG. 11" (21) which will be discussed later. Once the "Adaptable Multi-Procedural Sharps Safety Device's" "Injection Needle" "FIG. 1" (6) has been withdrawn from the patient during and injection procedure, the safety device will automatically "activate" moving into a "closed" and "active" position. Multiple prominently marked bio-hazard warning symbols will be displayed at this point in numerous locations on the exterior of the "Adaptable Multi-Procedural Sharps Safety Device". This serves to warn the user that the device is now dangerous medical waste but is safely secured and ready for appropriate disposal.

Explanation of FIG. 2 Illustration Numbers and their Corresponding Arrows

1. Syringe Barrel with Threading for Luer Tip

Note: For further information on "Syringe Barrel with Treading for a Luer Tip" see the "Explanatory Notes" for "FIG. 1" (1).

9. Luer Tip Attachment

As has been previously noted, the "Syringe Barrel with Threading for a Luer Tip" (1) is a readily available type of "Syringe Barrel" (8) in use in the medical profession today. "Syringe Barrels" (8) of this variety can be found in 1, 3, 5, 10-, 20-, 30- and 60-mL sizes as well as other more unique sizes for specialized medical procedures. The "Adaptable Multi-Procedural Sharps Safety Device" will also be able to attach to any mL size of "Syringe Barrel with Threading for a Luer Tip" (1).

Note: For further information on "Syringe Barrel with Threading for Lure Tip" see the "Explanatory Notes" for "FIG. 1" (1).

2. Interlocking Teeth in the Closed Position

"FIG. 2" illustrates the "Adaptable Multi-Procedural Sharps Safety Device" in the "closed" post-injection position. The safety device has "activated" causing the "Interlocking Teeth" "FIG. 1" (2), "Flange that the Sharp Passes Through" (5), and "Flexible Sharps Containment Chamber" (3) to move forward and lock into place. In the depiction in "FIG. 2" the "Interlocking Teeth" (2) have snapped and inter-locked together actively preventing the two sides of the "Flexible Sharps Containment Chamber" (3) from separating. This keeps the chamber sealed and air-tight, preventing sharps injury from occurring while also sealing any potential blood-borne pathogens from leaking externally. The "Interlocking Teeth" (2) are one of the most integral components of the "Adaptable Multi-Procedural Sharps Safety Device". The patterns found on the bottom of the "Interlocking Teeth" (2) interlink with each other when the safety device is in the "active" and "closed" position effectively preventing each side from pulling apart from each other. The pattern found on the bottom of the "Interlocking Teeth" (2) also contain smaller closures, which, when pressed together, securely snap into place. The pattern design found on the "Interlocking Teeth" (2) will vary depending on the kind of sharp being enclosed as well as its size and shape to assure maximum closure strength and effectiveness. The primary purpose of the "Interlocking Teeth" "FIG. 1" (2) is to prevent the two sides of the safety device from pulling apart. This function will effectively prevent re-use of the "Adaptable Multi-Procedural Sharps Safety Device" effectively eliminating a persistent health risk in the world today which is medical device, or in this case syringe, re-use.

Note: For further information on "Interlocking Teeth" see the "Explanatory Notes" for "FIG. 1" (2).

5. Flange that the Sharp Passes Through

Note: For further information on the "Flange that the Sharp Passes Through" see the "Explanatory Notes" for "FIG. 1" (5).

5. Flange is Hollow Allowing for Sharp to Pass Through

The "Flange" (5) contains a hollow cavity in which the "Injection Needle" "FIG. 1" (6) or as will be examined later, "Scalpel Blade" "FIG. 11" (21) passes through during the closure process. Friction or resistance could affect the operation of the safety device in a way which could cause injury to the person receiving the injection, blood withdraw, or other medical procedure. Therefore, the "Flange" (5) has two primary purposes. First, it keeps the safety device from touching or interfering with the sharp such as the "Injection Needle" "FIG. 1" (6) or "Scalpel Blade" "FIG. 11" (21). Second, the "Flange" (5) acts as a central locus of the "Adaptable Multi-Procedural Sharps Safety Device" in which multiple components interconnect. For instance, the "Interlocking Teeth" "FIG. 1" (2), "Leaf Springs" "FIG. 1" (7) and "Flexible Sharps Containment Chamber" (3) are all connected to the "Flange" (5) and depend on it for structural integrity, stability, strength, as well as agility. One important feature to note is that the "Flange{'s}" (5) internal and external shape and contours may vary by the sharp being enclosed. This is necessary due to the technical parameters of the specific sharp the device is containing. For instance, the needs of an "Injection Needle" "FIG. 1" (6) are far different than those of a "Scalpel Blade" "FIG. 11" (21) therefore the shape of the "Flange" (5) would need to be altered accordingly to accommodate the unique characteristics of the sharp being contained.

Note: For further information on the "Flange that the Needle Passes Through" see the "Explanatory Notes" for "FIG. 1" (5).

7. Leaf Spring

Note: For further information on the "Leaf Spring" see the "Explanatory Notes" for "FIG. 1" (7).

See also: For further information on the "Cut Away of Leaf Spring" see the "Explanatory Notes" for "FIG. 3" (7).

3. Flexible Sharps Containment Chamber

Note: For further information on the "Flexible Sharps Containment Chamber" see the "Explanatory Notes" for "FIG. 1" (3).

8. Syringe Barrel

Note: For further information on "Syringe Barrels" see the "Explanatory Notes" for "FIG. 1" (8).

See also: For information on "Luer Tip Attachments" see the "Explanatory Notes" for "FIG. 2" (9).

Explanatory Notes for FIG. 3

Safety Device Motion Illustration—Shown Connected to a Luer Tip Syringe Barrel

The notes and discussions on this page refer to the drawing labeled, "FIG. 3". "FIG. 3" is numbered 1, 3, 4, 5, 7, 8 and 10. The numbers are placed throughout the illustration. They are associated with corresponding arrows which point to various sections and aspects of the drawing which need further explanation. This methodology allows for a clear and explanation of the various sections and sub-sections of the mechanism.

Description of FIG. 3

In "FIG. 3" the "Adaptable Multi-Procedural Sharps Safety Device" is shown in three different stages. The first stage reveals the "Safety Device [in the] "Open" Pre-Injection" (10) position. At this point, no injection or medical procedure has taken place and the safety device remains in a stand-by position and the "Injection Needle" "FIG. 1" (6) is unobstructed and ready to initiate a medical procedure.

The second stage shows the "Safety Device [is in the] Closing Post-Injection" (10) position. In this phase, the injection or medical procedure has already taken place and the safety device has automatically triggered activating the safety device to enclose the "Injection Needle" "FIG. 1" (6) or as will be discussed later, the "Scalpel Blade" "FIG. 11" (21) In this instance, the "Leaf Springs" (7) are automatically becoming unflexed while simultaneously, the "Flange" (5) is quickly moving forward toward the tip of the "Injection Needle" "FIG. 1" (6)".

Finally, the third and final stage in the process illustrates that the "Safety Device is "Closed" (10) following the medical procedure and the "Adaptable Multi-Procedural Sharps Safety Device" is ready for safe disposal. In this phase, the "Injection Needle" "FIG. 1" (6) is enclosed within the "Flexible Sharps Containment Chamber" (3), the "Leaf Springs" (7) are in their natural "unflexed" and "closed" position and the "Flange" (5) has completely moved forward. At this point, the internal passage of the "Flange" (5) is completely obstructed and internally sealed off by the "Flexible Sharps Containment Chamber" (3). Although not depicted in "FIG. 3", the "Interlocking Teeth" are also permanently locked together at this time helping to prevent accidental exposure, injury, and re-use of the device.

Also illustrated within "FIG. 3" is a "Cut Away of [the] "Leaf Spring" (7) which depicts the rounded shape of the spring. The "Leaf Spring" (7) may take various other shapes and sizes to accommodate different types of sharps to be enclosed, however, the depiction in "FIG. 3" (7) expresses the most common format to be used. The "Leaf Spring" (7) is integral to the function of the "Adaptable Multi-Procedural Sharps Safety Device" and will be made of a "Shape Memory Alloy" or other material with the unique characteristics of "Shape Memory". The springs will be embedded within the "Strong Flexible Plastic" (4) or other highly durable yet flexible material.

Explanation of FIG. 3 Illustration Numbers and their Corresponding Arrows

5. Flange

In the illustration the "Flange" (5) is shown in the "closed" post-injection position. As previously mentioned in "FIGS. 1" and "FIG. 2" the "Flange" (5) is responsible for two vital purposes. First, providing a safe passage for the "Injection Needle" "FIG. 1" (6) or as will be discussed "Scalpel Blade" "FIG. 11" (21) to pass through unobstructed and without interference. Second, the "Flange" (5) provides overall structural integrity to many of the elements of the "Adaptable Multi-Procedural Sharps Safety Device" such as the "Leaf Springs" (7) and the "Flexible Sharps Containment Chamber" (3). The "Flange" (5) also enables the "Adaptable Multi-Procedural Sharps Safety Device" to smoothly move into the "open" and "closed" position. Another important purpose of the "Flange" (5) is to protect the individual performing the medical procedure as well as anyone else in the vicinity from sharps injury as the sharp is being encased within the "Adaptable Multi-Procedural Sharps Safety Device". As the "Flange" (5) quickly moves forward as the device is activated the sharp is shielded guarding against potential injury until the safety device is completely "closed".

Note: For further information on the "Flange that the Sharp Passes Through" see "Explanatory Notes" for: "FIG. 1" (5) and "FIG. 2" (5).

4. Strong Flexible Plastic

Note: For further information on the "Flexible Plastic" see "Explanatory Notes" for: "FIG. 1" (4).

5. Flange

Note: For information on the "Flange that the Sharp Passes Through" see "Explanatory Notes" for: "FIG. 1" (5), "FIG. 2" (5), and "FIG. 3" (5).

4. Regions of the External Surface is Textured

Areas of the "Adaptable Multi-Procedural Sharps Safety Device" are textured to reinforce the surface making it more durable and flexible. This additional plastic will help prevent the sharp from having the ability to puncture through the plastic. It will also provide a more durable medium for the "Flexible Sharps Containment Chamber" to be embedded in while also helping the plastic maintain its form as the device flexes "open" and "closed".

3. Flexible Sharps Containment Chamber

Note: For further information on the "Flexible Sharps Containment Chamber" see "Explanatory Notes" for: "FIG. 1" (3).

7. Leaf Springs

Note: For further information on the "Leaf Spring" see "Explanatory Notes" for: "FIG. 1" (7).

1. Luer Tip Connection

Note: For further information on the "Syringe Barrel with Threading for Luer Tip" see "Explanatory Notes" for: "FIG. 1" (1) and "Luer Tip Attachment" "FIG. 2" (9).

8. Syringe Barrel

Note: For further information on the "Syringe Barrel" see "Explanatory Notes" for: "FIG. 1" (8).

7. Cutaway of Leaf Spring

In this depiction, the "Leaf Spring" (7) is rounded in diameter and runs the full length of the safety device both above and beneath the "Flexible Sharps Containment Chamber" (3). One important note though, the spring may be molded into several different forms, shapes, and lengths to fulfil the appropriate flexing function of the "Adaptable Multi-Procedural Sharps Safety Device".

Note: For further information on the "Leaf Spring" see "Explanatory Notes" for: "FIG. 1" (7).

7. Leaf Springs

Note: For further information on the "Leaf Spring" see "Explanatory Notes" for: "FIG. 1" (7).

10. Safety Device in the Open Pre-Injection Position

In this illustration, the "Adaptable Multi-Procedural Sharps Safety Device" is in the "open" pre-injection position. At this stage, the safety device is "flexed" "open", meaning the "Leaf Springs" (7) are now arched, while the "Flange" (5) and "Flexible Sharps Containment Chamber" (3) have retracted to fully expose the "injection Needle" "FIG. 1" (6). The safety device is now standing-by in the pre-activation position during the medical procedure.

10. Safety Device Closing Post-Injection

In the illustration, the "Adaptable Multi-Procedural Sharps Safety Device" has started the process of moving toward the "closed" position following a medical procedure. The safety device is beginning to "un-flex" which means the "Leaf Springs" (7) are now beginning to return to their naturally "un-flexed" state while the "Flange" (5) and "Flexible Sharps Containment Chamber" (3) which had previously been retracted to expose the "Injection Needle" "FIG. 1" (6), or as previously mentioned, "Scalpel Blade" "FIG. 11" (6) now are rapidly moving forward to enclose the sharp. At this stage the "Injection needle" "FIG. 1" (6) or "Scalpel Blade" "FIG. 11" (21) are beginning to be enclosed within the "Adaptable Multi-Procedural Sharps Safety Device".

10. Safety Device Closed

This illustration shows the "Adaptable Multi-Procedural Sharps Safety Device" in the "closed" position. The safety device has completely "un-flexed" and enclosed the "Injection Needle" "FIG. 1" (6) or "Scalpel Blade" "FIG. 11" (21) within the "Flexible Sharps Containment Chamber" (3) and the "Leaf Springs" (7) are in their naturally "un-flexed" state. Additionally, the "Flange" (5) has moved forward beyond the tip of the sharp completely securing and enclosing the sharp and its potentially bio-hazardous contents inside the puncture, leak, and tamper proof "Flexible Sharps Containment Chamber" (3).

8. Syringe

Note: For further information on the "Syringe Barrel with Threading for Luer Tip" see "Explanatory Notes" for: "FIG. 1" (1).

See also: For further information on the "Syringe Barrel" see "Explanatory Notes" for: "FIG. 1" (8).

For further information on the "Luer Tip Attachment" see "Explanatory Notes" for: "FIG. 2" (9).

Explanatory Notes for FIG. 4

Safety Device Front Perspective with Side-View Cut-Away

The notes and discussions on this page refer to the drawing labeled, "FIG. 4". "FIG. 4" is numbered 2, 3, 4 5, 6, and 7. The numbers are placed throughout the illustration. They are associated with corresponding arrows which point to various sections and aspects of the drawing which need further explanation. This methodology allows for a clear and explanation of the various sections and sub-sections of the mechanism.

Description of FIG. 4

In "FIG. 4" the "Adaptable Multi-Procedural Sharps Safety Device" is examined from the perspective of the "Front Cutaway without [the] Flange", "Front with [the] Flange" as well as the "Side Cutaway of [the] Front Region of [the] Safety Device". The first perspective labeled; "Front with Flange" shown on the right details the front perspective of the "Adaptable Multi-Procedural Sharps Safety Device" with the "Flange" "FIG. 1" (5) attached. The drawing illustrates the interior of the "Flexible Sharps Containment Chamber" "FIG. 1" (3) following and injection or medical procedure in the "closed" position. At that point, the chamber, and the "Flange" "FIG. 1" (5) is sealed off preventing sharps injury or fluid leakage. Once the safety device is activated the "Injection Needle" "FIG. 1" (6), or as will be detailed later the "Scalpel Blade" "FIG. 11" (21), is safely enclosed and no longer accessible and the device is ready for safe disposal. Additionally, the "Interlocking Teeth" (2) as visible in the illustration are tightly sealed and clamped "closed". The diagram also reveals that the "Flange is Concaved Inward" (5). As previously mentioned, the "Flange" "FIG. 1" (5) assures that the sharp can pass through the safety device without interference during a medical procedure yet is also partially responsible overall device stability since so many of the safety device's components are connected to it. The concaved nature of the "Flange" "FIG. 1" (5) assures that no part of the device touches the sharp during a medical procedure by allowing free passage of the sharp to travel through whether in the "open" or "closed" position. The "Flange's" "FIG. 1" (5) shape and dimensions will vary according to the kind of sharp it is enclosing. For instance, an "Injection Needle" "FIG. 1" (6) would have different dimensions and lengths than a "Scalpel Blade" "FIG. 11" (21) therefore the "Flange" "FIG. 1" (5) would need to have slightly different dimensions and shape as well to accommodate the sharp.

The third illustration labeled; "Side Cutaway of Front Region of Safety Device" shows the "Adaptable Multi-Procedural Sharps Safety Device" in the "Closed" position as viewed from the side perspective. The "Injection Needle" "FIG. 1" (6) can be seen enclosed within the puncture-proof, leak-proof, and tamper-proof "Flexible Sharps Containment Chamber" (3) following an injection. Simultaneously, the "Flange Passage for the Sharp" (5) has been sealed off by the closing of the "Flexible Sharps Containment Chamber" (3) and the "Leaf Springs" (7) and returned to their natural "unflexed" state.

The third illustration labeled; "Front Cutaway without Flange" details a partial view of the "Adaptable Multi-Procedural Sharps Safety Device" from the forward perspective without the "Flange" (5). The "Leaf Springs" (7) are visible embedded within the "Strong Flexible Plastic" (4) which not only helps provide structural integrity but also agility when bending. The "Strong Flexible Plastic" (4) also serves another vital purpose because it encompasses the "Interlocking Teeth" (2) on the underside as well as the "Flexible Sharps Containment Chamber" (3) in the center position.

Explanation of FIG. 4 Illustration Numbers and their Corresponding Arrows

2. Interlocking Teeth

The illustration depicted in "FIG. 4" (2) shows the interlocking effect of the "Adaptable Multi-Procedural Sharps Safety Device" once the device is "closed" following a medical procedure. The teeth will come in a variety of different patterns which will vary based on the sharp to be enclosed. Once both sides of the safety device are "active" and brought into contact with each other the "Interlocking Teeth" "FIG. 1" (2) permanently lock together causing resistance to each other. The more tension applied the "Interlocking Teeth" "FIG. 1" (2) the greater their resistance. Once interlocked they will never unlock. This helps prevent the safety device from being re-used.

Note: For further information on the "Interlocking Teeth" see "Explanatory Notes" for: "FIG. 1" (2) and "FIG. 2" (2).

3. Chamber Closed Post-Injection

Once the "Flexible Sharp Containment Chamber" "FIG. 1" (3) has closed following a medical procedure the sharp contained inside is no longer is accessible or visible. From that point, the sharp is permanently sealed within the chamber where any blood-borne pathogens or residual medications are safely and permanently sealed inside. Additionally, the chamber is puncture proof so any risk of the "Injection Needle" "FIG. 1" (6) or the "Scalpel Blade" "FIG. 11" (21) accidentally cutting through the chamber is alleviated. Once the "Flexible Sharps Containment Chamber" "FIG. 1" (3) is fully enclosing the sharp the entire "Adaptable Multi-Procedural Sharps Safety Device" is "active" guarding against accidental injury preventing re-use. At this point the unit can never be reused.

Note: For further information on the "Flexible Sharps Containment Chamber" see "Explanatory Notes" for: "FIG. 1" (3).

5. Flange is Concaved Inward

Figure 11:
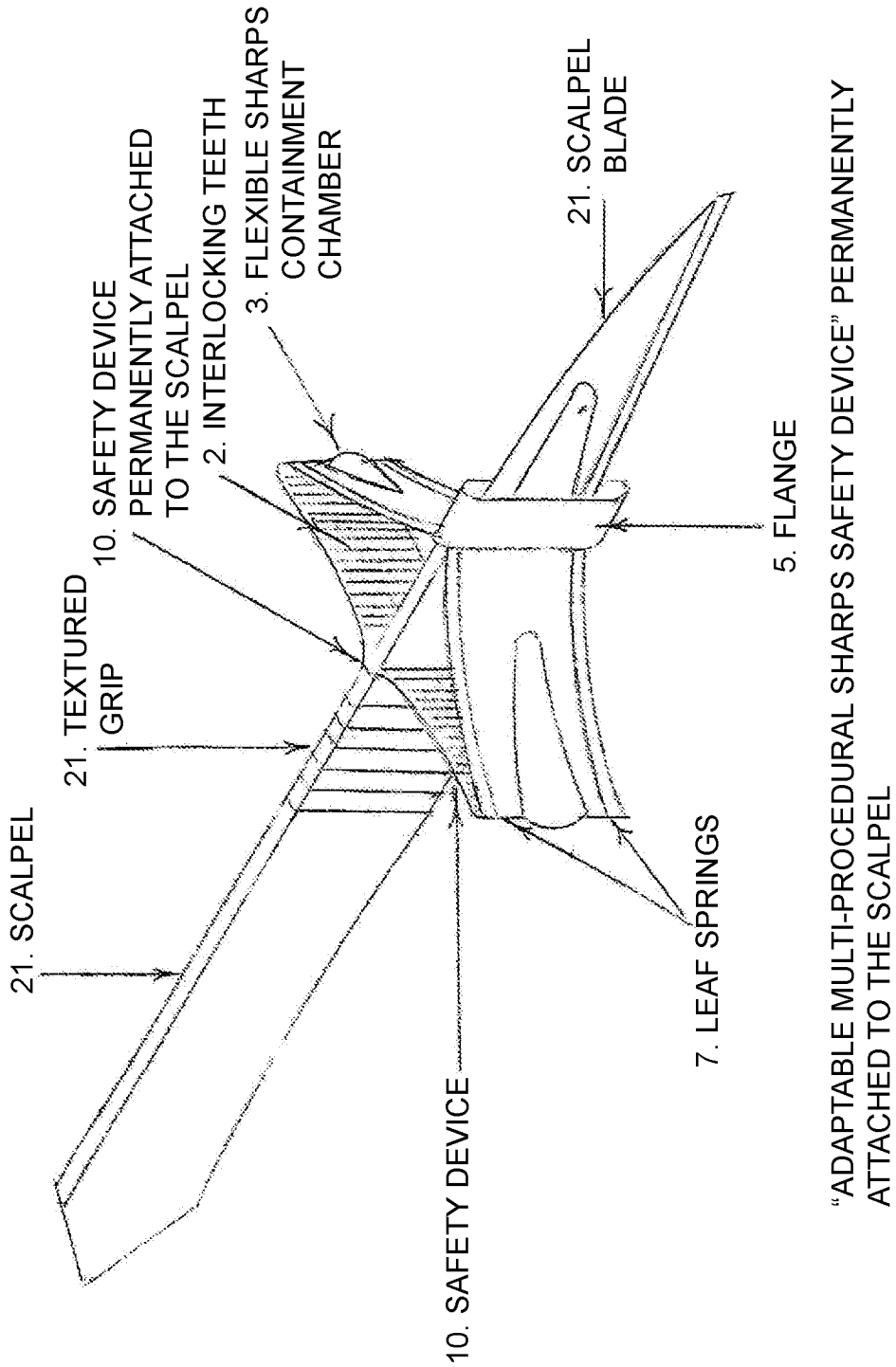
FIG. 11 shows a perspective view of a sharps safety device according to at least one embodiment of the present disclosure.

The "Flange" "FIG. 1" (5) is concaved inward allowing the "Injection Needle" "FIG. 1" (6) or "Scalpel Blade" "FIG. 11" (21) to pass through the "Adaptable Multi-Procedural Sharps Safety Device" without interference. The shape and dimension of the "Flange" (5) will vary based upon the sharp being enclosed within the safety device. Additionally, once the "Adaptable Multi-Procedural Sharps Safety Device" is "closed" and "active" bio-hazard warning labels will be prominently displayed warning that the device currently contains bio-hazardous waste and must be disposed of appropriately.

Note: For further information on the "Flange" see "Explanatory Notes" for: "FIG. 1" (5) and "FIG. 2" (5).

5. Flange

Note: For further information on the "Flange" see "Explanatory Notes" for: "FIG. 1" (5) and "FIG. 2" (5).

7. Leaf Spring Embedded within Plastic

The "Leaf Spring" "FIG. 1" (7) is manufactured and molded within "Strong Flexible Plastic" "FIG. 1" (4) which not only helps to maintain the device's overall structural integrity holding the "Leaf Springs" "FIG. 1" (7) in place but also helps the springs "open" and "close" in unison and at a controlled rate of speed.

Note: For further information on the "Leaf Spring" see "Explanatory Notes" for: "FIG. 1" (7).

6. Injection Needle Contained within Chamber Post-Injection

Note: For information on "Safety Device Closed" see "Explanatory Notes" for: "FIG. 3" (10).

2. Interlocking Teeth

Note: For further information on the "Interlocking Teeth" see "Explanatory Notes" for: "FIG. 1" (2) and "FIG. 2" (2).

5. Flange Passage for Needle

Note: For information on the "Flange that the Sharp Passes Through" see "Explanatory Notes" for: "FIG. 1" (5) and "FIG. 2" (5).

5. Flange

Note: For information on the "Flange" see "Explanatory Notes" for: "FIG. 1" (5), "FIG. 2" (5), and "FIG. 3" (5).

3. Flexible Sharp Containment Chamber

Note: For further information on the "Flexible Sharp Containment Chamber" see "Explanatory Notes" for: "FIG. 1" (3).

7. Leaf Springs

Note: For further information on the "Leaf Spring" see "Explanatory Notes" for: "FIG. 1" (7).

4. Strong Flexible Plastic

Note: For further information on the "Flexible Plastic" see "Explanatory Notes" for: "FIG. 1" (4).

2. Interlocking Teeth

Note: For further information on the "Interlocking Teeth" see "Explanatory Notes" for: "FIG. 1" (2) and "FIG. 2" (2).

7. Leaf Springs

Note: For further information on the "Leaf Spring" see "Explanatory Notes" for: "FIG. 1" (7).

6. Injection Needle Cutaway

This drawing labeled "Front Cutaway without Flange" illustrates a cross section of the "Adaptable Multi-Procedural Sharps Safety Device" with the "Injection Needle" "FIG. 1" (6) contained inside. For clarity, the illustration does not include the "Flange" "FIG. 1" (5), "FIG. 2" (5), "FIG. 3" (5). Once the safety device is "active" the "Injection Needle" "FIG. 1" (6) is safely and permanently sealed within the "Flexible Sharps Containment Chamber" "FIG. 1" (3) and the internal entrance of the "Flange" "FIG. 1" (5), "FIG. 2" (5), "FIG. 3" (5) which normally allows the "Injection Needle" "FIG. 1" (6) or as will be examined later the "Scalpel Blade" "FIG. 11" (21) to pass through unobstructed suddenly becomes sealed off and obstructed by the "Flexible Sharps Containment Chamber" "FIG. 1" (3) and locked in place by the "Interlocking Teeth" (2).

Note: For further information on the "Injection Needle" see "Explanatory Notes" for: "FIG. 1" (6).

4. Strong Flexible Plastic

Note: For further information on the "Flexible Plastic" see "Explanatory Notes" for: "FIG. 1" (4).

Explanatory Notes for FIG. 5

Adaptable Multi-Procedural Sharps Safety Device Rear Perspective

The notes and discussions on this page refer to the drawing labeled, "FIG. 5". "FIG. 5" is numbered 1, 2, 3, 4, 5, 6, 7, 11, and 12. The numbers are placed throughout the illustration. They are associated with corresponding arrows which point to various sections and aspects of the drawing which need further explanation. This methodology allows for a clear and explanation of the various sections and sub-sections of the mechanism.

Description of FIG. 5

"FIG. 5" examines the "Adaptable Multi-Procedural Sharps Safety Device [from the] Rear Perspective". The diagram on the right mentions the "Adaptable Multi-Procedural Sharps Safety Device with optional Pre-Filled Orphan Pac" for the first time. While the "Pre-filled Orphan Pac" "FIG. 9" (17) will be examined in detail later in this document a brief explanation is necessary at this point. The "Pre-filled Orphan Pac" "FIG. 9" (17) is a drug delivery apparatus specific designed as an integral component of the "Adaptable Multi-Procedural Sharps Safety Device" that the individual administering the medical procedure has the option to use. When the individual opts to utilize the "Pre-filled Orphan Pac" "FIG. 9" (17) they merely need to select the medication variety as well as dosage amount that they need and thread the "Pre-filled Orphan Pac" "FIG. 9" (17) onto the "Adaptable Multi-Procedural Sharps Safety Device" with the appropriate size and type of "Injection Needle" "FIG. 1" (6). They may also opt to use an "Adaptable Multi-Procedural Sharps Safety Device with optional Pre-Filled Orphan Pac" that is already permanently attached if they wish. In this case the appropriate needle would already be attached to the device. As previously mentioned, the "Adaptable Multi-Procedural Sharps Safety Device" is highly adaptable in nature accommodating not only "Pre-filled Orphan Pac's" "FIG. 9" (17) as discussed previously, "Syringe Barrels with Threading for Luer Tips" as mentioned in "FIG. 1" (1), "Syringe Barrels" permanently attached to the safety device as mentioned in "FIG. 1" (8), or even "Scalpel Blades" and "Scalpels" as mentioned in as mentioned in "FIG. 11" (21). Versatility is one of the "Adaptable Multi-Procedural Sharps Safety Device" greatest advantages.

As the illustrations note, the "Pre-filled Orphan Pac" "FIG. 9" (17) has more than one option available for threading onto the "Adaptable Multi-Procedural Sharps Safety Device," First, it can attach utilizing a "Luer Tip Connection" (1) as seen in the diagram on the left in which the safety device attaches to the "Pre-filled Orphan Pac" "FIG. 9" (17) using standard "Luer Tip Threading." However, the user also has the option of threading the "Pre-filled Orphan Pac" "FIG. 9" (17) onto the "Adaptable Multi-Procedural Sharps Safety Device" using a more robust external threading on the "Pre-Filled Orphan Pac" "FIG. 9" (17) itself. The benefit in this case is a more secure connection during the drug delivery process which would be advantageous in certain circumstances.

The "Adaptable Multi-Procedural Sharps Safety Device" shown in both illustrations is in the "open" pre-procedure phase. In this case, the "Injection Needle" "FIG. 1" (6) is fully exposed because the "Flange" "FIG. 1" (5), "Flexible Sharps Containment Chamber" "FIG. 1" (3), "Interlocking Teeth" "FIG. 1" (2) and "Leaf Springs" "FIG. 1" (7) are all in a retracted position to allow for an injection or other medical procedure. Once "activated" the "Adaptable Multi-Procedural Sharps Safety Device" will stay "open" until the medical procedure has taken place then will automatically "close" following the procedure.

An important feature of the "Adaptable Multi-Procedural Sharps Safety Device" which is visible in both illustrations is a "Mesh Filter to Prevent [the] Passage of Air Bubbles [from] Passing through the Syringe or Pre-Filled Orphan Pac to [the] Patient During [an] Injection" (11). Air bubbles passing into the patient from the drug delivery device during a medical procedure poses a significant threat to the patient's safety. To diminish this threat the "Adaptable Multi-Procedural Sharps Safety Device" for "Injection Needles" "FIG. 1" (6) has a mesh filter measuring in certain number of microns which will eliminate potential air bubbles contained within the "Syringe Barrel" FIG. 1" (8) or "Pre-Filled Orphan Pac" "FIG. 9" (17) from passing from the device to the patient during an injection or medical procedure. The "Pre-Filled Orphan Pac" "FIG. 9" (17) also has a secondary mesh filter built in as an additional screening process to eliminate risk.

Explanation of FIG. 5 Illustration Numbers and their Corresponding Arrows

6. Injection Needle

The "Injection Needles" "FIG. 1" (6) metal gauges and needle lengths vary widely depending on the needs of the medical procedure. For instance, needle gauges and lengths which are typically used in the medical field today are: 22 gauge with needle lengths between 1 to 1½ inches in length; 23 gauge with needle lengths 1 inch in length; 26 gauge with needle lengths ½ inch in length; 27 gauge with needle lengths ½ inch in length; 22 gauge with needle lengths 1 inch in length; 25 gauge with needle lengths between 1½ inches to ⅝ inches in length; 18 gauge with needle lengths 1 inch in length; 30 gauge with needle lengths ½ inch in length, and 20 gauge with needle lengths 1 inch in length. This is but a few of the lengths and gauges of "Injection Needles" "FIG. 1" (6) that the "Adaptable Multi-Procedural Sharps Safety Device" will be able to accommodate. Additionally, the individual administering the medical procedure may decide to select a "Adaptable Multi-Procedural Sharps Safety Device" with the "Injection Needle" "FIG. 1" (6) already permanently embedded within the safety device. In this instance, the user simply selects a safety device with the appropriate length and gauge of needle that they wish to use and thread it onto a "Syringe Barrel" FIG. 1" (8) or "Pre-Filled Orphan Pac" "FIG. 9" (17) of their choice. However, they may opt to select a "Adaptable Multi-Procedural Sharps Safety Device" with a widened "Flange" (5) in which they may select the appropriate length and gauge of readymade "Luer Tip or Luer Tip Slip" "Injection Needle" "FIG. 1" (6) that they wish to use and simply insert it through the "Flange" (5) and thread it onto internal "Luer Threading" contained within the safety device. Every required "Injection Needle" "FIG. 1" (6) length and gauge used for medical procedures will be accommodated with the "Adaptable Multi-Procedural Sharps Safety Device". The same will be true for "Scalpel Blades" "FIG. 11" (21) which will be discussed beginning in "FIG. 11".

Note: For further information on the "Injection Needle" see "Explanatory Notes" for: "FIG. 1" (6).

5. Flange

Note: For information on the "Flange" see "Explanatory Notes" for: "FIG. 1" (5), "FIG. 2" (5), and "FIG. 3" (5).

4. External Surface is Textured

Note: For information on the "Regions of the External Surface is Textured" see "Explanatory Notes" for: "FIG. 3" (4).

12. Safety Device Treaded for Pre-Filled Orphan Pac

The "Adaptable Multi-Procedural Sharps Safety Device" as portrayed in the illustration labeled, "Safety Device Threaded for [a] Pre-Filled Orphan Pac" shows an alternative form of external threading available for the "Pre-Filled Orphan Pac" "FIG. 9" (17). This threading is more robust than the standard Luer Connection threading method and will provide a more solid connection to the "Adaptable Multi-Procedural Sharps Safety Device" which in turn will enhance the devices overall safety. However, as has been explained previously the "Adaptable Multi-Procedural Sharps Safety Device with optional Pre-Filled Orphan Pac" will also be able to be threaded onto the safety device utilizing a "Luer Tip Connection" (1). Additionally, the "Adaptable Multi-Procedural Sharps Safety Device with optional Pre-Filled Orphan Pac" may also be permanently attached to each other. In this instance the "Injection Needle" "FIG. 1" (6) as already permanently embedded within the "Adaptable Multi-Procedural Sharps Safety Device" and all the user needs to do is select the medication type and dosage level that they need in order to administer the injection.

11. Mesh Filter to Prevent Passage of Air Bubbles Passing Through the Syringe or Pre-Filled Orphan Pac to Patient During Injection As previously explained, a potentially life-threatening risk during an injection or other drug delivery process is air bubbles passing from the medical device into the patient's blood stream. To mitigate this risk the "Adaptable Multi-Procedural Sharps Safety Device" has a "Mesh Filter to Prevent [the] Passage of Air Bubbles [from] Passing through the Syringe or Pre-Filled Orphan Pac to [the] Patient During [an] Injection" (11) The mesh fine filter measuring in a specific number of microns will eliminate potential air bubbles from traveling through the safety device into the patient during the procedure. A similar one will also be present inside the "Pre-Filled Orphan Pac" "FIG. 9" (17) assembly as an enhanced level of security.

3. Flexible Sharps Containment Chamber

Note: For further information on the "Flexible Sharps Containment Chamber" see "Explanatory Notes" for: "FIG. 1" (3).

7. Leaf Spring

Note: For further information on the "Leaf Spring" see "Explanatory Notes" for: "FIG. 1" (7) "FIG. 3" (7).

2. Interlocking Teeth

Note: For further information on the "Interlocking Teeth" see "Explanatory Notes" for: "FIG. 1" (2) and "FIG. 2" (2).

11. Mesh Filter Measuring in the Microns

Note: For further information on the "Mesh Filter to Prevent Passage of Air Bubbles Passing through the Syringe or Pre-Filled Orphan Pac to Patient During Injection" see "Explanatory Notes" for: "FIG. 5" (11).

1. Luer Tip Connection

Note: For further information on the "Luer Tip Connection" see "Explanatory Notes" for: "FIG. 1" (1) and "Luer Tip Attachment" "FIG. 2" (1, 9).

4. External Surface is Textured

Note: For information on the "Regions of the External Surface is Textured" see "Explanatory Notes" for: "FIG. 3" (4).

3. Flexible Sharps Containment Chamber

Note: For further information on the "Flexible Sharps Containment Chamber" see "Explanatory Notes" for: "FIG. 1" (3).

6. Injection Needle

Note: For further information on the "Injection Needle" see "Explanatory Notes" for: "FIG. 1" (6).

5. Flange

Note: For information on the "Flange" see "Explanatory Notes" for: "FIG. 1" (5), "FIG. 2" (5), and "FIG. 3" (5).

2. Interlocking Teeth

Note: For further information on the "Interlocking Teeth" see "Explanatory Notes" for: "FIG. 1" (2) and "FIG. 2" (3).

7. Leaf Spring

Note: For further information on the "Leaf Spring" see "Explanatory Notes" for: "FIG. 1" (7) "FIG. 4" (7).

Explanatory Notes for FIG. 6

Ball and Socket Joint and Connection Between Safety Device and Pre-Filled Orphan Pac The notes and discussions on this page refer to the drawing labeled, "FIG. 6". "FIG. 6" is numbered 1, 13, 14, and 16. The numbers are placed throughout the illustration. They are associated with corresponding arrows which point to various sections and aspects of the drawing which need further explanation. This methodology allows for a clear and explanation of the various sections and sub-sections of the mechanism.

Description of FIG. 6

In this diagram, the "Ball and Socket Joint and Connection Between the Safety Device and the optional Pre-Filled Orphan Pac" is examined. The "Ball Joint Connection to the Joint Socket" (13) enables the individual administering the injection or medical procedure to manually adjust the angle of the "Adaptable Multi-Procedural Sharps Safety Device with optional Pre-Filled Orphan Pac" to any angle within 180 degrees for maximum ergonomic comfort as well as accessibility to the patient. This agility will allow any region of the patient to be easily accessible whether they are standing, sitting, or laying down. However, one important point to note, no matter how many degrees of rotation that the "Ball Joint Connection to the Joint Socket" (13) moves, the "Fluid Channel to the Pre-Filled Orphan Pac" (14) never becomes constricted thus allowing efficient delivery of medications. Additionally, the motion of the "Ball Joint Connection to the Joint Socket" (13) is not loose but rather a controlled movement in a series of adjustments due allowing for a safe stable delivery of medications. For the injection procedure to take place the "Ball Joint Connection to the Joint Socket" (13) must be locked into place by pressing a built-in lock which will prevent the "Ball Joint Connection to the Joint Socket" (13) from moving once the medical procedure begins. This action will prevent a loss of control of the "Adaptable Multi-Procedural Sharps Safety Device and optional Pre-Filled Orphan Pac" during an injection as well as prevent patient injury from such an occurrence.

The "External Fluid Channel to the Pre-Filled Orphan Pac" (14) is attached to the "Ball Joint" portion of the "Ball Joint Connection to the Joint Socket" (13) which is in turn directly connected to the "Pre-Filled Orphan Pac" shown in the "FIG. 9" (17). The "External Fluid Channel to the Pre-Filled Orphan Pac" (14) is the passage that the medications travel through during an injection procedure. As the medication moves toward the patient it passes through a second fine mesh filter which is similar to the one found in the "Adaptable Multi-Procedural Sharps Safety Device." The purpose of the filter is also the same, to prevent air bubbles passing from the "Adaptable Multi-Procedural Sharps Safety Device and optional Pre-Filled Orphan Pac" into the patient.

The socket portion of the "Ball Joint Connection to the Joint Socket" (13) directly attaches to the safety device by way of a "Luer Tip Connection" (1) or as previously noted utilizing "External Threading for [a] Non-Luer Tip Connection" (16). As previously mentioned, the "Adaptable Multi-Procedural Sharps Safety Device with optional Pre-Filled Orphan Pac" will also come as a single fused together unit that is pre-filled with a specific dosage of medication permanently attached to an "Injection Needle" "FIG. 1" (6).

Explanation of FIG. 6 Illustration Numbers and their Corresponding Arrows

13. Ball Joint Rotation 180° Degrees Up-Down and 180° Right-Left

Figure 7:
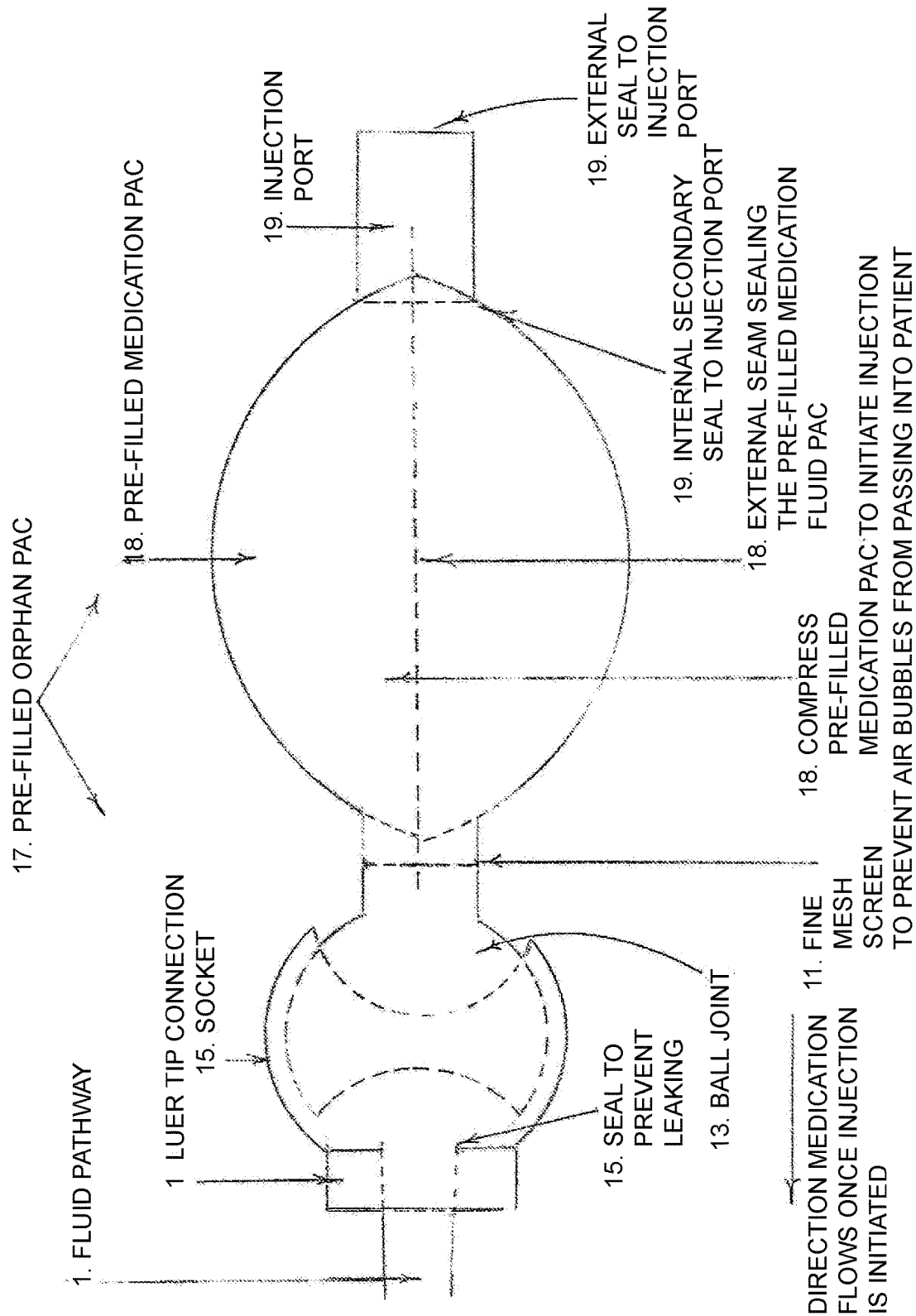
FIG. 7 shows features of a sharps safety device according to at least one embodiment of the present disclosure.

The "Ball Joint Connection to the Joint Socket" (13) is an integral part of the "Pre-Filled Orphan Pac" "FIG. 7" (17) and provides a wide range of flexibility when joined to the "Adaptable Multi-Procedural Sharps Safety Device." The individual administering the injection or medical procedure has the ability to manually adjust the angle of the "Adaptable Multi-Procedural Sharps Safety Device with optional Pre-Filled Orphan Pac" to any angle within a 180 degrees radius enabling easy and safe access to the patient situated in virtually and position while simultaneously providing ergonomic comfortable to the user. However, before the medical procedure can begin the user must lock the "Ball Joint Connection to [the] Joint Socket" (13) into place. This protects the individual administering the injection as well as the patient by preventing the device from moving out of position during and injection procedure.

1. External Fluid Channel to Pre-Filled Orphan Pac

The "External Fluid Channel to the Pre-Filled Orphan Pac" (14) runs through the "Ball Joint Connection within the Joint Socket" (13) and into the "Pre-Filled Orphan Pac" "FIG. 7" (17). Although the "Ball Joint Connection within the Joint Socket" (13) can rotate in any direction within 180 degrees the fluid channel will never become obstructed or pinched due to rotation because at all times the channel will remain the same diameter internally allowing medications to move freely through the "Adaptable Multi-Procedural Sharps Safety Device with optional Pre-Filled Orphan Pac" to the patient. As the medication travels through the "External Fluid Channel to the Pre-Filled Orphan Pac" (14) it will pass through a second ultra-fine mesh filter contained within the channel. This filter serves the same purpose as the "Mesh Filter to Prevent [the] Passage of Air Bubbles [from] Passing through the Syringe or Pre-Filled Orphan Pac to [the] Patient During [an] Injection" as illustrated in "FIG. 5" (11) within the "Adaptable Multi-Procedural Sharps Safety Device" which is, to alleviate any potentially hazardous air bubbles contained within the medication in "Pre-Filled Orphan Pac" "FIG. 9" (17) from travelling into the patient during an injection procedure. Air-bubbles can also obstruct the flow of medication and prevent it from moving forward so removal of these bubbles is vital to the function of the device. These filters will eliminate the common injection practice of "flipping" the "Syringe Barrel" "FIG. 1" (8) to try to cause air bubbles to dissolve before administering the injection which is a practice that frequently creates more air-bubbles.

16. External Threading for Non-Luer Tip Connection

One important aspect of the "Adaptable Multi-Procedural Sharps Safety Device with optional Pre-Filled Orphan Pac" is its versatility. For instance, the "Adaptable Multi-Procedural Sharps Safety Device" may be attached to the "Pre-Filled Orphan Pac" "FIG. 7" (17) by way of "Internal Threading for [a] Luer Tip Connection" which can be seen in (1). Another method of attachment the "Pre-Filled Orphan Pac" "FIG. 7" (17) may utilize to attached to the "Adaptable Multi-Procedural Sharps Safety Device" is a more robust "External Threading for [a] Non-Luer Tip Connection" which can be seen in (16). In this case, the connection is significantly more secure to assure that leakage and accidental exposure is prevented. One important note. Once the "Pre-Filled Orphan Pac" "FIG. 9" (17) is connected to the "Adaptable Multi-Procedural Sharps Safety Device" using either "Internal Threading for [a] Luer Tip Connection" (1) or "External Threading for [a] Non-Luer Tip Connection" (16) the attachment becomes permanent due to a brake barrier built into the threading which prevents removal once completely threaded on to the device.

Note: For information on "This Version of Safety Device Threaded for Orphan Pac" see "Explanatory Notes" for: "FIG. 5" (12).

1. Internal Threading for Luer Tip Connection

Note: For information on the "Syringe Barrel with Threading for Lure Tip" see "Explanatory Notes" for: "FIG. 1" (1).

See also: For information on the "Luer Tip Attachment" see "Explanatory Notes" for: "FIG. 2" (9).

For information on "External Threading for Non-Luer Tip Connection" and "Internal Threading for Luer Tip Attachment" see "Explanatory Notes" for: "FIG. 6" (13,1).

1. Luer Tip Connection

Note: For information on the "Syringe Barrel with Threading for Lure Tip" see "Explanatory Notes" for: "FIG. 1" (1).

See also: For information on the "Luer Tip Attachment" see "Explanatory Notes" for: "FIG. 2" (9).

15. Socket

The "Socket" (15) which is a part of the "Ball Joint Connection to the Joint Socket" (13) assembly serves an important purpose because it provides mobility to the "Pre-Filled Orphan Pac" "FIG. 9" (17) as well as the "Adaptable Multi-Procedural Sharps Safety Device" The "Ball Joint" (13) moves freely within the "Joint Socket" as seen in (15) to assume any position within a 180-degree radius. By possessing either a "Luer Tip Connection" (1), "External Threading for Non-Luer Tip Connection" (16), or a permanent connection, the "Ball Joint Connection to the Joint Socket" (13) pairs together the "Pre-Filled Orphan Pac" "FIG. 9" (17) to the "Adaptable Multi-Procedural Sharps Safety Device" allowing it to work as a singular unit.

1. Luer Tip Connection

Note: For information on the "Syringe Barrel with Threading for Lure Tip" see "Explanatory Notes" for: "FIG. 1" (1).

For information on the "Luer Tip Attachment" see "Explanatory Notes" for: "FIG. 2" (2).

13. Ball Joint Connection to Joint Socket

The "Ball Joint Connection to the Joint Socket" (13) allows the "Ball Joint" (13) to freely move in any direction within a 180-degree radius within the "Socket" (15). The "Ball Joint" (13) is also connected to the "External Fluid Channel to the Pre-Filled Orphan Pac" (14) which is in turn directly attached to the "Pre-Filled Orphan Pac" "FIG. 9" (17). During an injection procedure with the medication moves through "Pre-Filled Orphan Pac" "FIG. 9" (17) to the "Ball Joint Connection to the Joint Socket" (13) and on to the "Adaptable Multi-Procedural Sharps Safety Device" on its way to the patient. Once the injection procedure starts the "Ball Joint Connection to the Joint Socket" (13) becomes rigid to prevent accidental movement during the procedure. This assures patient safety as well as the safety of the individual administering the injection.

Explanatory Notes for FIG. 7

Side View Cut-Away of Pre-Filled Orphan Pac Assembly Including Socket and Ball Joint The notes and discussions on this page refer to the drawing labeled, "FIG. 7". "FIG. 7" is numbered 1, 11, 13, 15, 17, 18, and 19. The numbers are placed throughout the illustration. They are associated with corresponding arrows which point to various sections and aspects of the drawing which need further explanation. This methodology allows for a clear and explanation of the various sections and sub-sections of the mechanism.

Description of FIG. 7

"FIG. 7" examines the "Side View Cutaway of the Pre-Filled Orphan Pac Assembly Including the Socket and Ball Joint" which is specifically designed for the "Adaptable Multi-Procedural Sharps Safety Device". As has been previously explained, the "Pre-Filled Orphan Pac" (17) contains a "Ball Joint" (13) and a "Socket" (15) assembly which provides the individual administering an injection the ability to adjust the "Adaptable Multi-Procedural Sharps Safety Device with optional Pre-Filled Orphan Pac" to any position within a 180-degree radius for optimal reach and ergonomic comfort. This capability also allows the medical professional or individual administering the injection effortless access to patients in a wide variety of positions where injections or medical procedures may have been difficult in the past.

Another important feature of the "Pre-Filled Orphan Pac" (17) is that it can be attached to the "Adaptable Multi-Procedural Sharps Safety Device" by way of a "Luer Tip Connection" (1) as displayed in this illustration or by "External Threading for a Non-Luer Tip Connection" as it appears in "FIG. 6" (16). This method of attachment is more robust and secure. Additionally, the "Pre-Filled Orphan Pac" (17) may also be manufactured permanently attached to the "Adaptable Multi-Procedural Sharps Safety Device". In this instance, the "Pre-Filled Orphan Pac" (17) will already be paired with the appropriate "Injection Needle" "FIG. 1" (6) gauge and length and the individual administering the injection will only need to select the desired medication and dosage level needed.

The "Socket" (15) and "Ball Joint" (13) are attached to the "External Fluid Channel to the Pre-Filled Orphan Pac" "FIG. 6" (14) and in turn the "Fluid Channel" is attached to the "Medication Fluid Pac" (18). Within the "External Fluid Channel to the Pre-Filled Orphan Pac" "FIG. 6" (14) is a "Fine Mesh Screen to Prevent Air Bubbles from Passing into the Patient" (11) during an injection or medical procedure. This ultra-fine mesh filter is similar to the "Mesh Filter to Prevent [the] Passage of Air Bubbles [from] Passing through the Syringe or Pre-Filled Orphan Pac to [the] Patient During [an] Injection" which appears in "FIG. 5" (11). The mesh filter measuring in the microns will eliminate potential air bubbles from traveling through the "Pre-Filled Orphan Pac" (17) into the patient during the procedure. The ability to remove air-bubbles during the injection process significantly increases the safety of the injection and removes the need for the individual to attempt to remove air bubbles manually.

The "Pre-Filled Medication Fluid Pac" (18) which is the fluid containing portion of the "Pre-Filled Orphan Pac" (17) contains a precisely measured dose of a specific medication. The "Pre-Filled Orphan Pac" (17)" can be pre-loaded with any medication available and in any dosage size desired by the individual administering the injection. For instance, if a medical professional had a specific type of medication in mind for their patient and they were going to administer a dosage of 0.25 mL based upon the statistics of the patient, they would select a "Pre-Filled Orphan Pac" (17) that was pre-filled with the medication and the dosage size (in this case 0.25 mL) and administer the injection.

The "Ball Joint" (13) and "Socket" (15) allows the individual administering the injection to adjust the "Adaptable Multi-Procedural Sharps Safety Device" to any position within 180° degrees to allow for a safe and efficient injection.

The "Adaptable Multi-Procedural Sharps Safety Device with Pre-Filled Orphan Pac" also contains an "External Injection Port" (19) which allows a medical professional the option of adding additional medications into the "Medication Fluid Pac" (18) if necessary. Once the injection process has begun the individual administering the medical procedure simply needs to compress the "Medication Fluid Pac" (18) until all fluid is removed from the unit. Once the contents of the "Medication Fluid Pac" (18) has been fully manually compressed the "Medication Fluid Pac" (18) safely collapses inward into the bottom portion of the bubble of the "Medication Fluid Pac" (18). At this point the injection is complete, and once the user begins to withdraw the "Injection Needle" FIG. 1" (6) from the injection site of the patient the "Adaptable Multi-Procedural Sharps Safety Device" automatically begins "activating" and moving into the "Closed" position. At the completion of this step the "Adaptable Multi-Procedural Sharps Safety Device" permanently disables the device preventing injury and re-used.

Explanation of FIG. 7 Illustration Numbers and their Corresponding Arrows

17. Pre-Filled Medication Fluid Pac

The "Pre-Filled Medication Fluid Pac" (18) is where the "Pre-filled Orphan Pac's" (17) medication is stored until an injected is initiated. In order to perform an injection, the "Pre-Filled Medication Fluid Pac" (18) simply needs to be compressed utilizing pressure applied with the fingers on the front and the back of the "Pre-Filled Medication Fluid Pac" (18) simultaneously. As the cavity containing the medication collapses from the pressure being applied by the individual administering the injection the medication evacuates the cavity and moves forward through the "External Fluid Channel of the Orphan Pac" "FIG. 6" (14). As it continues forward it passes through the "Fluid Pathway" (1) and ultimately through the "Adaptable Multi-Procedural Sharps Safety Device" and then into the patient. If there arises the need to add additional medications into the "Pre-Filled Medication Fluid Pac" (18) the individual administering the injection can do so by utilizing the "Injection Port" (19) adding the additional medication via another syringe. At the completion of the injection the "Pre-Filled Medication Fluid Pac" (18) remains fully collapsed thus preventing re-use.

19. External Injection Port

The "External Injection Port" (19) is present in case the medical professional administering the injection needs to add additional medications to the "Pre-Filled Orphan Pac" (17). Since knowledge of drug compatibility would be necessary before carrying out this procedure the "Injection Port" (19) is primarily intended for a medical professional's use since some medications are incompatible and consultation of medical reference texts will likely be necessary to prevent patient injury. In order to deliver additional medication into the "Pre-Filled Medication Fluid Pac" (18) the additional medication is simply injected into the "Injection Port" (19) by way of another syringe which then adds the contents directly into the "Pre-Filled Medication Fluid Pac" (18) where it awaits the injection procedure. The "Injection Port" (19) design prevents any fluids whether medication or otherwise from leaking out of the port by keeping the port sealed at all times.

19. External Primary Seal to Injection Port

The "External Primary Seal to the Injection Port" (19) is the air-tight, leak-proof, exterior seal of the "External Injection Port" (19) which as has been previously noted is the location where additional medications may be added to the "Pre-Filled Medication Fluid Pac" (18). An injection directly into the "External Injection Port" (19) will add the additional medication into the "Pre-Filled Medication Fluid Pac" (18). Once the injection is complete the "External Primary Seal to the Injection Port" (19) as well as the "Internal Secondary Seal to the Injection Port" (19) which will be made of a material which will allow a "Injection Needle" "FIG. 1" (6) to pass through but prevent fluids from flowing out will reseal the injection point preventing any medications from leaking out of the "External Injection Port" (19).

19. Internal Secondary Seal to Injection Port

The "Internal Secondary Seal to the Injection Port" (19) is the sealed, air-tight, leak-proof interior seal of the "External Injection Port" (19) which serves as a secondary barrier to prevent the "Pre-Filled Medication Fluid Pac" (18) from leaking after an injection of additional medications through the "External Injection Port" (19).

18. External Seam Sealing the Pre-Filled Medication Fluid Pac

The "External Seam Sealing the Pre-Filled Medication Fluid Pac" (18) is one of many manufactured seams which help to assure the stability, structural integrity, flexibility, and performance of the "Pre-Filled Medication Fluid Pac" (18). The seams appearing on the "Pre-Filled Medication Fluid Pac" (18) not only seal in the contents and prevent leakage they also act as a joint which allows the "Pre-Filled Medication Fluid Pac" (18) to be gently compressed with the individual administering the injections fingers during an injection process. As pressure to the "Pre-Filled Medication Fluid Pac" (18) is applied the medication is delivered to the patient gently and at a regulated rate. The seams allow this process to take place without causing damage to the "Pre-Filled Medication Fluid Pac".

18. Compress Pre-Filled Orphan Pac to Initiate Injection

To initiate an injection with the "Pre-Filled Orphan Pac" (18) the individual administering the injection merely needs to compress the "Pre-Filled Medication Fluid Pac" (18) containing the medication with fingers using inward pressure on either side of the "Pre-Filled Medication Fluid Pac" (18). Once this step has started the "Pre-Filled Medication Fluid Pac" (18) will gently collapse inward at a pace directly measurable to the amount of pressure applied. As pressure is applied the medication then moves forward and ultimately through the "Fluid Pathway" (1) and the "Adaptable Multi-Procedural Sharps Safety Device" and into the patient.

11. Fine Mesh Screen to Prevent Air Bubbles from Passing into Patient

Contained within the "External Fluid Channel to the Pre-Filled Orphan Pac" "FIG. 6" (14) is another "Fine Mesh Screen to Prevent Air Bubbles from Passing into the Patient" (11) which is similar to the "Mesh Filter to Prevent [the] Passage of Air Bubbles [from] Passing through the Syringe or Pre-Filled Orphan Pac to [the] Patient During [an] Injection" displayed in "FIG. 5" (11). The fine mesh filter measuring only in the microns helps to eliminate air bubbles that may be present in the "Pre-Filled Orphan Pac" (17) prior to an injection because as the medication passes through the fine mesh the air bubbles will be blocked from moving forward toward the "Injection Needle" "FIG. 1" (6). This step helps to protect the patient from potential harm presented by air bubbles passing into the bloodstream.

Note: For further information on the "Several Micron Thick Mesh to Prevent Passage of Air Bubbles Passing from Syringe or Orphan Pac to Patient During Injection" see "Explanatory Notes" for: "FIG. 5" (11).

13. Ball Joint

Note: For information on the "Ball Joint Rotation 180° Degrees Up-Down and 180° Right-Left" see "Explanatory Notes" for: "FIG. 6" (13).

See also: For information on the "Socket" see "Explanatory Notes" for: "FIG. 6" (15.). For information on the "Ball Joint Connection to Joint Socket" see "Explanatory Notes" for: "FIG. 6" (13).

15. Seal to Prevent Leaking

An optional small O-ring seal may be placed within the "Socket" (15) to help prevent air or fluid leakage from taking place between the "Pre-filled Orphan Pac" (18) and the "Adaptable Multi-Procedural Sharps Safety Device" connection. Such a seal would help assure a more secure connection between the two units.

1. Fluid Pathway

The "Fluid Pathway" (1) is the passage that the medications travel through as it passes from the "Pre-filled Orphan Pac" (17) to the "Adaptable Multi-Procedural Sharps Safety Device" and ultimately into the individual receiving the injection. The "Fluid Pathway" (1) is of the same basic design in all units whether they use "Luer Tip Connections", "Luer Tip Slip Connections" or "External Threading for Non-Luer Tip Connection" as was described in "FIG. 6" (16) which are specifically designed for the "Pre-filled Orphan Pac" (18).

1. Luer Tip Connection

Note: For information on the "Syringe Barrel with Threading for Lure Tip" see "Explanatory Notes" for: "FIG. 1" (1).

See also: For information on the "Luer Tip Attachment" see "Explanatory Notes" for: "FIG. 2" (9).

15. Socket

Note: For information on the "Ball Joint Connection to the Joint Socket" see "Explanatory Notes" for: "FIG. 6" (13).

17. Pre-Filled Orphan Pac

The "Pre-Filled Orphan Pac" (17) is a drug delivery method specifically designed to accommodate the "Adaptable Multi-Procedural Sharps Safety Device". It is comprised of the "Medication Fluid Pac" (18); the "Injection Port" (19); "External Fluid Channel to the Pre-Filled Orphan Pac" "FIG. 6" (14); "Ball Joint" (13); "Socket" (15); as well as either a "Luer Tip Connection" (1), "Luer Tip Slip Connection" or "External Threading for Non-Luer Tip Connection" "FIG. 6" (16). As the name implies, the "Pre-Filled Orphan Pac" (17) is pre-filled with a precisely measured dosage of a specific medication. As mentioned before if necessary the individual administering the injection can add additional medications to the "Medication Fluid Pac" (18) through the "Injection Port" (19). Due to the unique design of the "Pre-Filled Orphan Pac" (17) the entire contents of the "Pre-Filled Medication Fluid Pac" (18) is injected into the patient during the injection procedure with the use of slight finger pressure. As pressure is applied to the "Pre-Filled Medication Fluid Pac" (18) it starts to concave inward thus pressing all fluids from the "Pre-Filled Orphan Pac" (17). The vacuum within the "Pre-Filled Medication Fluid Pac" (18) assures the removal of all medication during the procedure. Once the injection is complete the entire "Pre-Filled Medication Fluid Pac" (18) fully collapsed inward into itself and cannot be refilled or re-used. The unit is then rendered secure and useless.

Figure 8:
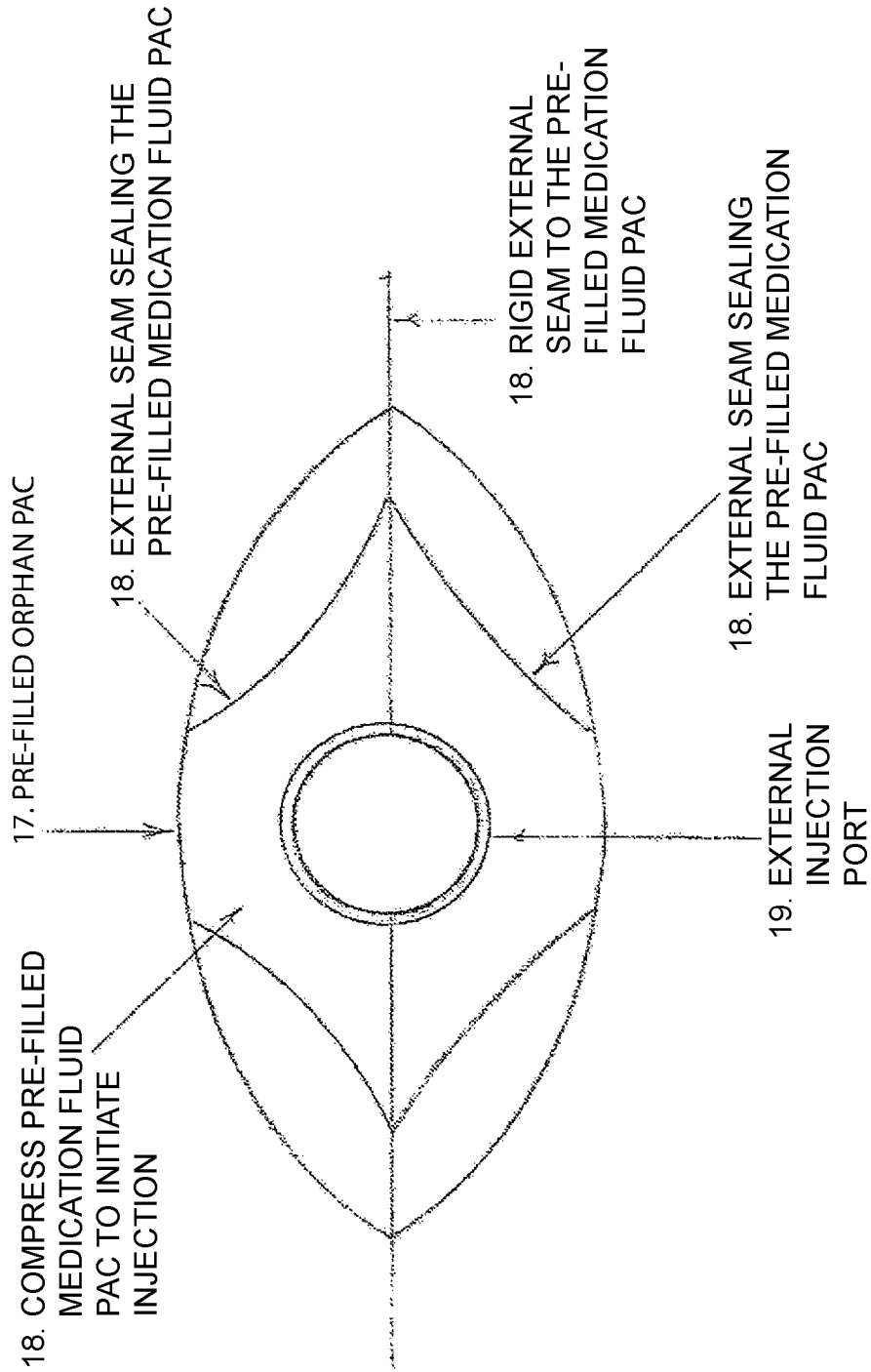
FIG. 8 shows a rear view of a sharps safety device according to at least one embodiment of the present disclosure.

Explanatory Notes for FIG. 8

Rear External View of the Pre-Filled Orphan Pac

The notes and discussions on this page refer to the drawing labeled, "FIG. 8". "FIG. 8" is numbered 17 thru 19 and the numbers are placed throughout the illustration. They are associated with corresponding arrows which point to various sections and aspects of the drawing which need further explanation. This methodology allows for a clear and explanation of the various sections and sub-sections of the mechanism.

Description of FIG. 8

The illustration in "FIG. 8" examines the "Rear External View of the Pre-Filled Orphan Pac". The upper region of the "Pre-Filled Orphan Pac" (17) shows the "Pre-Filled Medication Fluid Pac" "FIG. 7" (18). This is the location within the "Pre-Filled Orphan Pac" (17) that the individual initiating the injection compresses with their fingers or hand to initiate drug delivery to the patient. The bubble of the "Pre-Filled Medication Fluid Pac "FIG. 7" (18) is large enough to allow even a user with mobility complications such as Arthritis to easily perform the injection without undue stress or discomfort. Once fully compressed following the injection the "Pre-Filled Medication Fluid Pac "FIG. 7" (18) concaves inward and does not return to its original shape. This prevents reuse of the device. In addition to structural support for the "Pre-Filled Orphan Pac" (17) the "External Seams Sealing the Pre-Filled Medication Fluid Pac" (18) also act as joints providing the "Pre-Filled Medication Fluid Pac" "FIG. 7" (18) the ability to be compressed without breaking or leaking during the compression process of the injection procedure. The "External Seam[s] Sealing the Pre-Filled Medication Fluid Pac" (18) however, do not act as joints instead they provide overall rigidity to the structure of the "Pre-Filled Medication Fluid Pac" "FIG. 7" (18) since the upper portion of the bubble containing the medication collapses into the lower portion during the injection procedure. Once the injection is complete the top portion of the "Pre-Filled Medication Fluid Pac" "FIG. 7" (18) will remain collapsed into the bottom portion of the unit which prevents the device from being re-used. The "Rigid External Seams Sealing the Pre-Filled Medication Fluid Pac" (18) seal the outer edges of the "Pre-Filled Orphan Pac" (17) protecting the "Pre-Filled Medication Fluid Pac" "FIG. 7" (18), helping to seal in the contents, as well as providing a textured grip for the user to hold onto during the procedure. The "Rigid External Seams Sealing the Pre-Filled Medication Fluid Pac" (18) also fuses the flexible top portion of the "Pre-Filled Medication Fluid Pac" "FIG. 7" (18) to the more rigid bottom portion of the unit.

The "External Injection Port" (19) serves as a location for adding medication to the "Pre-Filled Medication Fluid Pac" "FIG. 7" (18) if the individual administering the injection needs to. If no additional medication needs to be added to the "Pre-Filled Medication Fluid Pac" "FIG. 7" (18) then the port remains sealed by the "Primary Seal to the External Injection Port" "FIG. 7" (19) which acts as a barrier prevent leakage of the internal contents and providing protection from the external environment outside of the "Pre-Filled Orphan Pac" (17).

Explanation of FIG. 8 Illustration Numbers and their Corresponding Arrows

17. Pre-Filled Orphan Pac
    Note: For information on the "Pre-Filled Orphan Pac" see "Explanatory Notes" for: "FIG. 7" (17).
    See also: For information on the "Pre-Filled Medication Fluid Pac" see "Explanatory Notes" for: "FIG. 7" (18).
18. External Seam Sealing the Pre-Filled Medication Fluid Pac
    Note: For information on the "External Seam Sealing the Pre-Filled Medication Fluid Pac" see "Explanatory Notes" for: "FIG. 7" (18).
18. Rigid External Seams Sealing the Pre-Filled Medication Fluid Pac
    Aside of providing structural support for the "Pre-Filled Medication Fluid Pac" "FIG. 7" (18) the "Rigid External Seams Sealing the Pre-Filled Medication Fluid Pac" (18) joins both the upper region of the "Pre-Filled Medication Fluid Pac" "FIG. 7" (18) bottom region. As the injection takes place the user will compress the upper region of the "Pre-Filled Medication Fluid Pac" "FIG. 7" (18) into the lower region utilizing light finger pressure. The "Rigid External Seams Sealing the Pre-Filled Medication Fluid Pac" (18) fuse both the upper and lower region of the "Pre-Filled Medication Fluid Pac" "FIG. 7" (18) together while also providing a more textured grip to be held onto during a medical procedure.
    Note: For information on the "External Seam Sealing the Pre-Filled Medication Fluid Pac" see "Explanatory Notes" for: "FIG. 7" (18).
18. External Seam Sealing the Pre-Filled Medication Fluid Pac
    Note: For information on the "External Seam Sealing the Pre-Filled Medication Fluid Pac" see "Explanatory Notes" for: "FIG. 7" (18).
19. External Injection Port
    Note: For information on the "External Injection Port" (19) see "Explanatory Notes" for: "FIG. 7" (19).
    See also: For information on the "Primary Seal to the Injection Port" see "Explanatory Notes" for: "FIG. 7" (19).
18. Compress Pre-Filled Orphan Pac to Initiate Injection
    Note: For information on the "Compress Pre-Filled Orphan Pac to Initiate Injection" see "Explanatory Notes" for: "FIG. 7" (18).
18. External Seam Sealing the Fluid Pac
    Note: For information on the "External Seam Sealing the Pre-Filled Medication Fluid Pac" see "Explanatory Notes" for: "FIG. 7" (18).

18. Rigid External Seams Sealing the Pre-Filled Medication Fluid Pac

Note: For information on the "Rigid External Seam Sealing the Pre-Filled Medication Fluid Pac" see "Explanatory Notes" for: "FIG. 8" (18).

See also: For information on the "External Seam Sealing the Pre-Filled Medication Fluid Pac" see "Explanatory Notes" for: "FIG. 7" (18).

Explanatory Notes for FIG. 9

Top View of "Adaptable Multi-Procedural Sharps Safety Device with Optional Pre-Filled Orphan Pac" Attached The notes and discussions on this page refer to the drawing labeled, "FIG. 9". "FIG. 9" is numbered 5, 6, 10, 13, 14, 15, 17, 18 and 19. The numbers are placed throughout the illustration. They are associated with corresponding arrows which point to various sections and aspects of the drawing which need further explanation. This methodology allows for a clear and explanation of the various sections and sub-sections of the mechanism.

Description of FIG. 9

In "FIG. 9" the overall perspective of the "Top View of [the] 'Adaptable Multi-Procedural Sharps Safety Device with Optional Pre-Filled Orphan Pac' Attached" is examined. The "Injection Needle" (6) with the "Adaptable Multi-Procedural Sharps Safety Device" (10) is visible and in the "open" and "in-active" pre-injection position. The "Leaf Springs" "FIG. 1" (7) are also in the "flexed" position. The "Flange" (5) can be seen in the illustration and is fully retracted exposing the "Injection Needle" (6). As is visible, the "Adaptable Multi-Procedural Sharps Safety Device" is shown attached to the "Pre-Filled Orphan Pac" (17) and is utilizing the "External Threading for [a] Non-Luer Tip Connection" "FIG. 6" (16). The "Ball Joint" (13) and its accompanying "Socket" (15) are present and has been previously mentioned provide the "Adaptable Multi-Procedural Sharps Safety Device with optional Pre-Filled Orphan Pac" (10,17) with the ability to move in any direction within 180° degrees. The "External Fluid Channel to the Pre-Filled Orphan Pac" (14) is not only interconnected to the "Ball Joint" (13) but also directly flows into the "Pre-Filled Medication Fluid Pac" "FIG. 7" (18) of the "Pre-Filled Orphan Pac" (17). This is the pathway that medication travels as it moves from the "Pre-Filled Medication Fluid Pac" "FIG. 7" (18) through the "Adaptable Multi-Procedural Sharps Safety Device" and ultimately to the patient during an injection. The "Rigid External Seams Sealing the Pre-Filled Medication Fluid Pac" (18) fuse both the upper and lower areas of the "Pre-Filled Medication Fluid Pac" "FIG. 7" (18) together. This is the region that the individual performing the medical procedure compresses utilizing hand or finger pressure during an injection. The "Rigid External Seams Sealing the Pre-Filled Medication Fluid Pac" (18) provides a textured grip for the user to hold onto during a medical procedure while also protecting the "Pre-Filled Medication Fluid Pac" "FIG. 7" (18) from external harm and fusing the top portion of the "Pre-Filled Medication Fluid Pac" "FIG. 7" (18) to the bottom.

The "Injection Port" (19) as seen in the diagram, is located at the posterior of the "Pre-Filled Orphan Pac" (17) and is present in case additional medications are deemed necessary to be added to the pre-loaded medications within the "Medication Fluid Pac" "FIG. 7" (18). The "Medication Name" (18) as well as the "Large Print Dosage Indicator" (18) are both located on the exterior of the "Medication Fluid Pac" "FIG. 7" (18). The same information is also printed in Braille for individuals with low vision who need visual assistance determining the medication type and dosage.

Explanation of FIG. 9 Illustration Numbers and their Corresponding Arrows

6. Injection Needle

Note: For further information on the "Injection Needle" see "Explanatory Notes" for: "FIG. 1" (6) and "FIG. 5" (6).

5. Flange

Note: For information on the "Flange" see "Explanatory Notes" for: "FIG. 1" (5), "FIG. 2" (5), and "FIG. 3" (5).

10. Adaptable Multi-Procedural Sharps Safety Device

Note: For further information on the "Safety Device in the Open Pre-Injection Position" see "Explanatory Notes" for: "FIG. 3" (10), "FIG. 3" "Safety Device Closing Post-Injection" (10), "FIG. 3" "Safety Device Closed" (10).

15. Socket

Note: For information on the "Socket" see "Explanatory Notes" for: "FIG. 6" (15), "FIG. 6" "Ball Joint Connection to the Joint Socket" (13).

13. Ball Joint

Note: For information on the "Ball Joint Rotation 180° Degrees Up-Down and 180° Right-Left" see "Explanatory Notes" for: "FIG. 6" (13), "FIG. 6" "Ball Joint Connection to Joint Socket" (13).

See also: For information on the "Socket" see "Explanatory Notes" for: "FIG. 6" (15).

18. Rigid External Seam Sealing the Pre-Filled Medication Fluid Pac

The rigid texturing in this region serves multiple purposes. First, it fuses both the top portion of the "Pre-Filled Medication Fluid Pac" "FIG. 7" (18) to the bottom portion together thus acting as a seal. Second, it helps to protect the "Pre-Filled Medication Fluid Pac" "FIG. 7" (18) from external damage. Third, it also provides a "steady grip" for the individual administering the injection to hold onto during an injection procedure. The shape and texturing visible in this illustration may vary from one "Pre-Filled Orphan Pac" (17) to another based upon the dosage size.

Note: For information on "External Seam Sealing the Pre-Filled Medication Fluid Pac" see "Explanatory Notes" for: "FIG. 7" (18).

See also: For information on the "Rigid External Seam Sealing the Pre-Filled Medication Fluid Pac" see "Explanatory Notes" for: "FIG. 8" (18).

18. Medication Name (Depiction is Hypothetical)

The "Medication Name" seen in (18) is hypothetical however, it accurately illustrates how the contents of the "Pre-Filled Medication Fluid Pac" "FIG. 7" (18) will be labeled. Additionally, the precise dosage will also be prominently displayed on the exterior of the "Pre-Filled Medication Fluid Pac" "FIG. 7" (18) in print that will be visible in low light environments. The depiction illustrates the prominence of the medical labeling on the "Pre-Filled Orphan Pac" (17). The same information will also be displayed in Braille for individuals administering injections with low vision. The exterior opposite side of the "Pre-Filled Medication Fluid Pac" "FIG. 7" (18) will contain data pertaining to the medication, as well as warnings, bar codes, emergency numbers, as well as other relevant information for the user.

18. Large Print Dosage Indicator (Depiction is Hypothetical)

As was previously noted each "Pre-Filled Orphan Pac" (17) will be prominently labeled with not only the "Medication Name" (18) as explained above but also the dosage in extra-large print and in a color that is clearly visible in any level of light. To aid individuals with visual difficulty all data including the "Medication Name" (18) and "Large Print Dosage Indicator" (18) will appear in Braille as well. This will assist low vision individuals who self-administer injections such as Diabetics. In this case they would use a "Pre-Filled Orphan Pac" (17) that contains insulin and a specific dosage.

19. External Injection Port

Note: For information on "External Injection Port" see "Explanatory Notes" for: "FIG. 7" (19), "Primary Seal to External Injection Port" "FIG. 7" (19).

17. Pre-Filled Orphan Pac

Note: For information on the "Pre-Filled Orphan Pac" see "Explanatory Notes" for: "FIG. 7" (17), "Pre-Filled Medication Fluid Pac" "FIG. 7" (18).

18. Pre-Filled Medication Fluid Pac

Note: For information on "Pre-Filled Medication Fluid Pac" see "Explanatory Notes" for: "FIG. 7" (18).

18. External Seam Sealing the Pre-Filled Medication Fluid Pac

Note: For information on the "External Seam Sealing the Pre-Filled Medication Fluid Pac" see "Explanatory Notes" for: "FIG. 7" (18), "Rigid External Seams Sealing the Pre-Filled Medication Fluid Pac" "Figure" 7 (18).

14. External Fluid Channel to the Pre-Filled Orphan Pac

Note: For information on the "External Fluid Channel to the Pre-Filled Orphan Pac" see "FIG. 6" (14).

Explanatory Notes for FIG. 10

Adaptable Multi-Procedural Sharps Safety Device with Optional Pre-Filled Orphan Pac and Pre-Use Injection Needle Cap The notes and discussions on this page refer to the drawing labeled, "FIG. 10". "FIG. 10" is numbered 1 thru 7 and the numbers are placed throughout the illustration. They are associated with corresponding arrows which point to various sections and aspects of the drawing which need further explanation. This methodology allows for a clear and explanation of the various sections and sub-sections of the mechanism.

Description of FIG. 10

In "FIG. 10" the "Adaptable Multi-Procedural Sharps Safety Device with Optional Pre-Filled Orphan Pac and Pre-Use Injection Needle Cap" is examined. The overall illustration is virtually identical to that of "FIG. 9" however, there is one key difference, that being, the "Pre-Use Injection Needle Cap" (20) which covers the "Injection Needle" "FIG. 1" (6). The "Pre-Use Injection Needle Cap" (20) is present on the "Adaptable Multi-Procedural Sharps Safety Device" before a medical procedure to assure the security of the Injection Needle as well as to provide a sterile environment for the "Injection Needle" "FIG. 1" (6).

The "Pre-Use Injection Needle Cap" (20) will cover the "Injection Needle" "FIG. 1" (6) of the "Adaptable Multi-Procedural Sharps Safety Device" prior to use to assure user safety and product sterility. However, there are four different methods that the cap will be attached to the safety device. In the first method, the "Pre-Use Injection Needle Cap" (20) will cover the "Injection Needle" "FIG. 1" (6) of the "Adaptable Multi-Procedural Sharps Safety Device" with the safety device in the "open" and "flexed" position. In this position the "Pre-Use Injection Needle Cap" (20) will be able to be easily removed from the "Adaptable Multi-Procedural Sharps Safety Device" by rotating to unthread the cap from exterior threading on the "Flange" "FIG. 1" (5) which will break a sterile seal. At that point the cap can be removed by gently pulling the cap off the device to fully expose the "Injection Needle" "FIG. 1" (6).

In the second method the "Pre-Use Injection Needle Cap" (20) required no rotation of the cap. The user will simply use a mild tugging motion to safely remove the cap from the "Adaptable Multi-Procedural Sharps Safety Device". Again, removal of the cap will result in breaking a sterile seal which assures the end-user that the "Adaptable Multi-Procedural Sharps Safety Device" has not been tampered with or used. In this case the cap will be attached to the "Flange" "FIG. 1" (5) but not via threading.

The third method of removal of the "Pre-Use Injection Needle Cap" (20) will be used when the user has opted to attach a pre-made "Luer Tip" or "Luer Slip Tip" "Injection Needle" "FIG. 1" (6) through the enlarged opening in the "Flange" "FIG. 1" (5) of the "Adaptable Multi-Procedural Sharps Safety Device." In this case, the cap will be shaped differently since the "Adaptable Multi-Procedural Sharps Safety Device" will have no "Injection Needle" "FIG. 1" (6) until the end-user inserts one into the "Adaptable Multi-Procedural Sharps Safety Device." In this case, the "Pre-Use Injection Needle Cap" (20) will simply be covering the open cavity of the "Flange" "FIG. 1" (5) which will be awaiting insertion of a "Injection Needle" "FIG. 1" (6). The "Pre-Use Injection Needle Cap" (20) will still need to be removed from the top of the "Flange" "FIG. 1" (5) either with a rotating motion to unthread the cap or a gentle tugging motion to detach the cap which will result in breaking a sterility seal.

The fourth method of removal of the "Pre-Use Injection Needle Cap" (20) will be different than the previous versions. In this instance, the "Adaptable Multi-Procedural Sharps Safety Device" will be in a partially "closed" and "unflexed" position however, the "Injection Needle" "FIG. 1" (6) will be fully enclosed, sterile, and secured within the "Adaptable Multi-Procedural Sharps Safety Device". At this point it will not be permanently locked. The "Pre-Use Injection Needle Cap" (20) will be attached to the cap by way of threading on the "Flange" "FIG. 1" (5). In this stage the "Adaptable Multi-Procedural Sharps Safety Device" will be in a dormant position. The Pre-Use Injection Needle Cap" (20) will again have a sterile seal to protect the environment of the "Injection Needle" "FIG. 1" (6) assuring the user the device has never been used. As previously noted, once the seal is broken the individual administering the medical procedure will clearly be able to see that the seal is broken. To activate the "Adaptable Multi-Procedural Sharps Safety Device" and remove the Pre-Use Injection Needle Cap" (20) the user performing the procedure will simply apply inward pressure onto the Pre-Use Injection Needle Cap" (20) which will cause the various components of the "Adaptable Multi-Procedural Sharps Safety Device" to move and set into "open" and "flexed" position. Once this step is completed the individual administering the procedure will rotate the Pre-Use Injection Needle Cap" (20) to detach it from threading on the "Flange" "FIG. 1" (5) resulting in breaking of the sterility seal then with light tugging motion pull the cap off the device exposing the "Injection Needle" "FIG. 1" (6). At this point the "Adaptable Multi-Procedural Sharps Safety Device" will be ready to perform the medical procedure. Once the injection or medical procedure is complete the "Adaptable Multi-Procedural Sharps Safety Device" will automatically move into the "unflexed" and "closed" position permanently enclosing the "Injection Needle" "FIG. 1" (6).

Explanation of FIG. 10 Illustration Numbers and their Corresponding Arrows

18. Medication Name (Depiction in Drawing is Hypothetical)

Note: For information on the "Medication Name" see "Explanatory Notes" for: "FIG. 9" (18).

18. Large Print Dosage Indicator (Depiction in Drawing is Hypothetical)

Note: For information on the "Large Print Dosage Indicator" see "Explanatory Notes" for: "FIG. 9" (18).

10. Adaptable Multi-Procedural Sharps Safety Device

Note: For further information on the "Safety Device in the Open Pre-Injection Position" see "Explanatory Notes" for: "FIG. 3" (10), "FIG. 3" "Safety Device Closing Post-Injection" (10), "FIG. 3" "Safety Device Closed" (10).

20. Pre-Use Injection Needle Cap

The "Pre-Use Injection Needle Cap" (20) covers the "Injection Needle" "FIG. 1" (6) on the "Adaptable Multi-Procedural Sharps Safety Device" and remains in place until the individual administering the medical procedure prepares the injection. Each "Pre-Use Injection Needle Cap" (20) contains an exterior sterility seal to protect it from exposure to outside contamination and to guarantee that the "Adaptable Multi-Procedural Sharps Safety Device" has never been used. The first format of the "Pre-Use Injection Needle Cap" (20) covering the "Adaptable Multi-Procedural Sharps Safety Device" will be to have the safety device in the "open" and "flexed" position. The "Injection Needle" "FIG. 1" (6) would be exposed in this case and the individual administering the injection or medical procedure would simply either rotate to unthread the "Pre-Use Injection Needle Cap" (20) from the "Adaptable Multi-Procedural Sharps Safety Device" which threads onto the exterior of the "Flange" "FIG. 1" (5) or gently pull on the cap to remove it from the "Adaptable Multi-Procedural Sharps Safety Device". Removal of the "Pre-Use Injection Needle Cap" (20) will result in breaking of the sterility seal. In either case the cap will be attached to the "Flange" "FIG. 1" (5) prior to removal to begin the medical procedure.

The second and third format of the "Pre-Use Injection Needle Cap" (20) will accommodate pre-made "Luer Tip" or "Luer Slip Tip" "Injection Needle" "FIG. 1" (6). In this case, a "Luer Tip" or "Luer Slip Tip" "Injection Needle" "FIG. 1" (6) will be manually inserted through a specially designed the "Flange" "FIG. 1" (5) with an enlarged opening specifically made to accommodate "Luer Tip" or "Luer Slip Tip" needles. Since the "Adaptable Multi-Procedural Sharps Safety Device" will not have "Injection Needle" "FIG. 1" (6) at this point until the individual administering the injection inserts one, the "Pre-Use Injection Needle Cap" (20) will be shaped differently and will cover the opening of the "Flange" "FIG. 1" (5). The "Pre-Use Injection Needle Cap" (20) will be removed from the exterior of the "Flange" "FIG. 1" (5) by unthreading the cap to loosen it from the "Flange" "FIG. 1" (5). This motion will break the sterility seal which will be clearly visible to the end-user.

The fourth format of the "Pre-Use Injection Needle Cap" (20) covering the "Injection Needle" "FIG. 1" (6) of the "Adaptable Multi-Procedural Sharps Safety Device" is more complicated in nature. In this case, the "Adaptable Multi-Procedural Sharps Safety Device" will appear to be closed, however, this will not be the case. It will be in a be in a pseudo "closed" and "unflexed" position. The "Injection Needle" "FIG. 1" (6) will be fully enclosed within the "Adaptable Multi-Procedural Sharps Safety Device" and the "Pre-Use Injection Needle Cap" (20) will be threaded onto the "Flange" "FIG. 1" (5). One key difference with this version of the cap will be that when the individual administering the medical procedure or injection is ready to initiate the procedure, they simply hold onto the "Pre-Use Injection Needle Cap" (20) and pulling the cap off they will press inward. This in turn will move the "Adaptable Multi-Procedural Sharps Safety Device" into a "open" and "flexed" and set position. The individual will then unthread the "Pre-Use Injection Needle Cap" to loosen the cap from the "Flange" "FIG. 1" (5). Again, a sterile seal will break and at this point the user will apply a slight pulling motion the cap to remove it. The "Injection Needle" "FIG. 1" (6) will be fully exposed. Once the medical procedure is finished the "Adaptable Multi-Procedural Sharps Safety Device" will automatically "close" and move into the "unflexed" position thus permanently sealing the "Injection Needle" "FIG. 1" (6) inside the "Adaptable Multi-Procedural Sharps Safety Device" safely containing any remaining contents inside.

13,15. Socket and Ball Joint

Note: For information on the "Socket" see "Explanatory Notes" for: "FIG. 6" (15), "FIG. 6" "Ball Joint Connection to the Joint Socket" (13).

18. Pre-Filled Medication Fluid Pac

Note: For information on the "Pre-Filled Medication Fluid Pac" see "Explanatory Notes" for: "FIG. 7" (18).

19. External Injection Port

Note: For information on "External Injection Port" see "Explanatory Notes" for: "FIG. 7" (19), "Primary Seal to External Injection Port" "FIG. 7" (19).

Explanatory Notes for FIG. 11

Scalpel with "Adaptable Multi-Procedural Sharps Safety Device" in the Open Pre-Use Position The notes and discussions on this page refer to the drawing labeled, "FIG. 11". "FIG. 11" is numbered 2, 3, 5, 7, 10, and 21. The numbers are placed throughout the illustration. They are associated with corresponding arrows which point to various sections and aspects of the drawing which need further explanation. This methodology allows for a clear and explanation of the various sections and sub-sections of the mechanism.

Description of FIG. 11

"FIG. 11" examines the "Scalpel with Adaptable Multi-Procedural Sharps Safety Device in the Open Pre-Use Position". The "Adaptable Multi-Procedural Sharps Safety Device" is a highly adaptable device and has been previously noted can accommodate both "Injection Needle[s]" "FIG. 1" (6) or "Scalpel Blade[s]" (21) as can be seen in "FIG. 11". The "Adaptable Multi-Procedural Sharps Safety Device" for the "Scalpel" (21) works virtually identically to the Safety Device for the "Injection Needle" "FIG. 1" (6). The differences are only minor, that being between in dimensions and shape. The reason for the minor differences is to accommodate the unique shape and size of the "Scalpel Blade" (21). However, components such as the "Interlocking Teeth" (2), "Flange" (5), "Leaf Spring[s]" (7), and "Flexible Sharps Containment Chamber" (3) operate identically in the "Adaptable Multi-Procedural Sharps Safety Device" that is designed for the "Injection Needle" "FIG. 1" (6).

Another minor difference can be in the pattern found on the underside of the "Interlocking Teeth" (2). Since the "Injection Needle" "FIG. 1" (6) and the "Scalpel Blade" (21) are different in size and shape the pattern found on the underside of the "Interlocking Teeth" (2) will have to be different as well to assure a tight and secure enclosure once the "Adaptable Multi-Procedural Sharps Safety Device" moves into the "active" and "closed" position.

The unique characteristics of the "Scalpel Blade" (21) will make it necessary to modify the "Flange" (5) size and shape to allow the "Scalpel Blade" (21) to freely travel through the "Flange" (5) during the "closing" procedure. Additionally, the length and shape of the "Leaf Spring[s]" (7) on the "Adaptable Multi-Procedural Sharps Safety Device" for the "Scalpel" (21) will make it necessary to modify their characteristics due to the distinctive needs of enclosing a "Scalpel Blade" (21) securely.

Finally, the "Flexible Sharps Containment Chamber" (3) will work identically to its counterpart enclosing the "Injection Needle" "FIG. 1" (6) and will be modified in size and shape to accommodate a "Scalpel Blade" (21). However, both the springs and the chamber will be made of a "Shape Memory Alloy" or other material with shape memory characteristics.

One unique distinction between the "Adaptable Multi-Procedural Sharps Safety Device" for the "Injection Needle" "FIG. 1" (6) and the "Scalpel Blade" (21) is that the individual using the "Adaptable Multi-Procedural Sharps Safety Device" for the "Scalpel" (21) will have strict control over when the "Adaptable Multi-Procedural Sharps Safety Device" "activates" to enclose the "Scalpel Blade" (21). The surgeon requires this level of control over the device to assure that the "Safety Device" (10) "activates" only when the medical procedure is completed since the timelines for this form of procedure is significantly different than that of an injection procedure.

Explanation of FIG. 11 Illustration Numbers and their Corresponding Arrows

21. Scalpel

The "Scalpel" (21) contains a sharp which, like the "Injection Needle" as seen in FIG. 1" (6) potentially carries bloodborne pathogens following a medical procedure.

The "Scalpel Blade" (21) is the point of contamination. To protect the medical professional performing surgery as well as the patient, the "Adaptable Multi-Procedural Sharps Safety Device" is designed to safely contain not only "Injection Needles" FIG. 1" (6) but also "Scalpel Blades" (21) which once activated safely encloses the blade or needle allowing for safe disposal.

21. Textured Grip

The "Textured Grip" (21) as displayed in the illustration allows the medical professional to maintain a firm steady grip on the "Scalpel" (21) throughout the medical procedure. The textured surface can be placed in many locations on the "Scalpel" (21) to prevent the device from slipping and injuring the patient or the medical professional.

10. Adaptable Multi-Procedural Sharps Safety Device Permanently Attached to the Scalpel The "Scalpel" (21), as seen in this diagram, contains the "Adaptable Multi-Procedural Sharps Safety Device" which is permanently attached. Each unit will have its own unique blade type and dimensions. The medical professional will simply select the necessary blade type for the surgical procedure. Once completed, the "Safety Device" (10) will automatically "close" becoming "active" permanently enclosing the "Scalpel Blade" (21).

Alternately, the "Adaptable Multi-Procedural Sharps Safety Device" will also have the option for a "Scalpel Blade" (21) to be permanently attached within the "Safety Device" (10). The attending physician will simply select the appropriate blade size and type embedded within the "Safety Device" (10) to perform the medical procedure and attach it to a compatible, ergonomically designed, "Scalpel" (21) handle with "Textured Grip" (21). Once the medical procedure is complete, the surgeon will "activate" the "Adaptable Multi-Procedural Sharps Safety Device" which will then permanently lock and enclose the "Scalpel Blade" (21) in the same manner as the "Adaptable Multi-Procedural Sharps Safety Device" encloses an "Injection Needle" "FIG. 1" (6). The "Safety Device" (10) will operate identically to the Safety Syringe and Needle Device and will permanently lock closed when activated.

2. Interlocking Teeth

The "Interlocking Teeth" (2) on the "Adaptable Multi-Procedural Sharps Safety Device" enclosing the "Scalpel" (21) operate identically to the "Adaptable Multi-Procedural Sharps Safety Device" enclosing an "Injection Needle" "FIG. 1" (6). The "Interlocking Teeth" (2) will permanently lock "closed" encasing the "Scalpel Blade" (21) once the "Safety Device" (10) has been "activated." The only difference is that the unit will be enclosing a "Scalpel Blade" (21) instead of a "Injection Needle" "FIG. 1" (6).

Note: For further information on the "Interlocking Teeth" see "Explanatory Notes" for: "FIG. 1" (2) and "FIG. 2" (2).

3. Flexible Sharps Containment Chamber

As explained the "Flexible Sharps Containment Chamber" (3) for the "Scalpel Blade" (21) operates identically to the "Flexible Sharps Containment Chamber" "FIG. 1" (3) for the "Injection Needle" "FIG. 1" (6). Once activated, the "Adaptable Multi-Procedural Sharps Safety Device" permanently will lock into the "closed" position "Scalpel Blade" (21) enclosed and sealed within the "Flexible Sharps Containment Chamber" (3). Any residual fluids remaining on the blade after the medial procedure will also be permanently contained within the puncture and leak proof chamber.

Note: For further information on the "Flexible Sharp Containment Chamber" see "Explanatory Notes" for: "FIG. 1" (3).

21. Scalpel Blade

"Scalpel Blade[s]" (21) come in a variety of sizes and shapes to accommodate specific surgical procedures. Each of these blade varieties will be available permanently embedded within a "Adaptable Multi-Procedural Sharps Safety Device" that has been paired with a "Scalpel Blade" (21). Once the surgeon selects the appropriate blade type the medical professional simply needs to snap the "Adaptable Multi-Procedural Sharps Safety Device" with the embedded "Scalpel Blade" (21) onto its ergonomically designed "Scalpel" (21) handle. At this point the device is ready to use.

Additionally, "Scalpel Blade[s]" (21) embedded into the "Adaptable Multi-Procedural Sharps Safety Device" that are permanently affixed to a "Scalpel" (21) handle will also be available depending on preference of the surgeon.

5. Flange

The "Flange" (5) as illustrated in "FIG. 11" operates identically to the "Flange" examined in "FIG. 1" (5) which accommodates "Injection Needles" "FIG. 1" (6). The versatility of the "Adaptable Multi-Procedural Sharps Safety Device" allows the device to enclose not only "Injection Needle[s]" "FIG. 1" (6) but also "Scalpel Blade[s]" (21). There are only minor variations in size and shape of the "Flange" (5) to allow the "Adaptable Multi-Procedural Sharps Safety Device" the "Scalpel Blade" (21) to travel through the "Flange" (5) during the enclosure process.

Note: For information on the "Flange" see "Explanatory Notes" for: "FIG. 1" (5), "FIG. 2" (5), and "FIG. 3" (5).

7. Leaf Spring

The "Leaf Spring" (7) as illustrated operates identically to the "Leaf Spring" which was detailed in "FIG. 1" (7) of the "Adaptable Multi-Procedural Sharps Safety Device" designed to enclose "Injection Needles" "FIG. 1" (6). Variations in size and shape and material composition of the "Leaf Spring" (7) will be necessary in this case to allow for safe and fast enclosure of the "Scalpel Blade" (21) once the surgeon completes the medical procedure and the safety device is "activated". The "Leaf Spring" (7) will be flexing to accommodate a larger area with the "Scalpel Blade" (21).

Note: For further information on the "Leaf Spring" see "Explanatory Notes" for: "FIG. 1" (7) "FIG. 3" (7).

10. Safety Device

As previously noted, the "Adaptable Multi-Procedural Sharps Safety Device for both the "Injection Needle" "FIG. 1" (6) and the "Scalpel" (21) function nearly identically. For instance, both versions have "Interlocking Teeth" (2), a "Flexible Sharps Containment Chamber" (3), a "Flange" (5), and "Leaf Spring[s]" (7) which all operate in the same manner. One obvious difference between the "Adaptable Multi-Procedural Sharps Safety Device that encloses the "Injection Needle" "FIG. 1" (6) and the "Scalpel" (21) is size and shape. Since a "Scalpel Blade(s)" (21) dimensions are significantly different from that of a "Injection Needle" "FIG. 1" (6) the measurements and shape of the "Flange" (5) must be different as well.

The "Adaptable Multi-Procedural Sharps Safety Device" for "Scalpel Blade[s]" (21) will come in two different varieties. In both cases the blade will be permanently embedded within the safety device. In one version of the "Adaptable Multi-Procedural Sharps Safety Device" for "Scalpel Blade(s)" (21) the surgeon will only have to select the containing a "Scalpel Blade" (21) of their choice. The surgeon then only needs to connect the unit onto its own ergonomically designed "Scalpel" (21) handle. The device is ready to use at this point.

The second variety of the "Adaptable Multi-Procedural Sharps Safety Device" for "Scalpel Blade[s]" (21) will also have a "Scalpel Blade" (21) embedded within the "Adaptable Multi-Procedural Sharps Safety Device" but in this case the safety device and blade will be permanently attached to its own ergonomically designed "Scalpel" (21) handle. In this case the surgeon merely needs to select the appropriate blade size and shape that they want to use for the medical procedure.

Note: For further information on the "Safety Device in the Open Pre-Injection Position" see "Explanatory Notes" for: "FIG. 3" (10), "FIG. 3" "Safety Device Closing Post-Injection" (10), "FIG. 3" "Safety Device Closed" (10).

Figure 12:
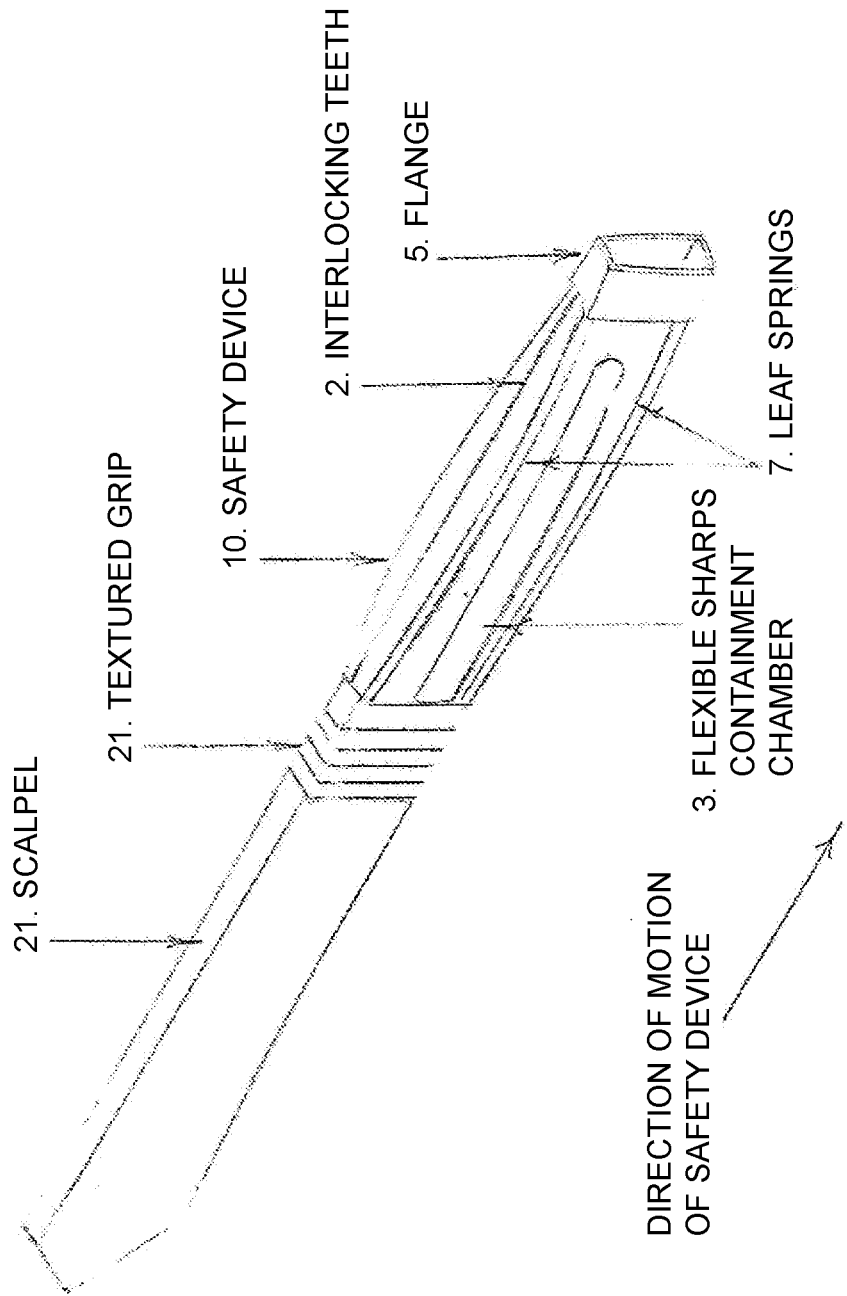
FIG. 12 shows a perspective view of a sharps safety device according to at least one embodiment of the present disclosure.

Explanatory Notes for FIG. 12

Scalpel with Adaptable Multi-Procedural Sharps Safety Device in the Closed Post-Use Position The notes and discussions on this page refer to the drawing labeled, "FIG. 12". "FIG. 12" is numbered 2, 3, 5, 7, 10, and 21. The numbers are placed throughout the illustration. They are associated with corresponding arrows which point to various sections and aspects of the drawing which need further explanation. This methodology allows for a clear and explanation of the various sections and sub-sections of the mechanism.

Description of FIG. 12

"FIG. 12" examines the Scalpel with the "Adaptable Multi-Procedural Sharps Safety Device" in the "Closed" Post-Use Position. Although similar to the description covered in "FIG. 11" the illustration as seen in "FIG. 12" has one key difference, that being the "Safety Device" (10) is shown in the "active" and permanently "closed" position. The "Leaf Springs" (7) in the drawing are visible in a resting and "unflexed" position as is the "Flexible Sharps Containment Chamber" (3). The "Flange" (5) has moved forward during this process internally sealing off and securing the "Scalpel Blade" "FIG. 11" (21). At this stage, the "Adaptable Multi-Procedural Sharps Safety Device" is permanently "closed" and locked, preventing external contact with the "Scalpel Blade" "FIG. 11" (21) from taking place. At this time, the user may safely dispose of the unit.

Explanation of FIG. 12 Illustration Numbers and their Corresponding Arrows

21. Scalpel

Note: For further information on the "Scalpel" see "Explanatory Notes" for: "FIG. 11" (21).

21. Textured Grip

Note: For further information on the "Textured Grip" see "Explanatory Notes" for: "FIG. 11" (21).

10. Safety Device

The "Safety Device" (10) as seen in this depiction is in the "closed" post-use position in which the "Scalpel Blade" "FIG. 11" (21) is safely secured within the "Flexible Sharps Containment Chamber" (3). The "Adaptable Multi-Procedural Sharps Safety Device" as shown closes in the identical manner as the "Adaptable Multi-Procedural Sharps Safety Device" seen in "FIG. 3" (10). Once the "Scalpel Blade" "FIG. 11" (21) is permanently enclosed within the "Flexible Sharps Containment Chamber" (3) it may be disposed of in an appropriate manner.

Note: For further information on the "Adaptable Multi-Procedural Sharps Safety Device Permanently Attached to the Scalpel" see "Explanatory Notes" for: "FIG. 11" (10).

See also: For related information on the "Safety Device in the Open Pre-Injection Position" see "Explanatory Notes" for: "FIG. 3" (10), "FIG. 3" "Safety Device Closing Post-Injection" (10), "FIG. 3" "Safety Device Closed" (10).

Interlocking Teeth Seam

The "Interlocking Teeth Seam" (2) as visible in this illustration, reveals the point where both sides of the "Interlocking Teeth" (2) press together and permanently snap shut the moment the "Safety Device" (10) is in the "active" and "closed" position. The "Scalpel Blade" "FIG. 11" (21) which is not visible is permanently enclosed within the "Flexible Sharps Containment Chamber" (3) and the device.

Note: For further information on the "Interlocking Teeth" see "Explanatory Notes" for: "FIG. 11" (2).

See also: For further information on the "Interlocking Teeth" see "Explanatory Notes" for: "FIG. 1" (2) and "FIG. 2" (2).

5. Flange

Note: For further information on the "Flange" see "Explanatory Notes" for: "FIG. 11" (5).

See also: For information on the "Flange" see "Explanatory Notes" for: "FIG. 1" (5), "FIG. 2" (5), and "FIG. 3" (5).

7. Leaf Springs

Note: For further information on the "Leaf Springs" see "Explanatory Notes" for: "FIG. 11" (7).
See also: For further information on the "Leaf Spring" see "Explanatory Notes" for. "FIG. 1" (7) "FIG. 3" (7).
3. Flexible Sharps Containment Chamber
Note: For further information on the "Flexible Sharps Containment Chamber" see "Explanatory Notes" for. "FIG. 11" (3).
See also: For further information on the "Flexible Sharps Containment Chamber" see "Explanatory Notes" for: "FIG. 1" (3).

Figure 13:
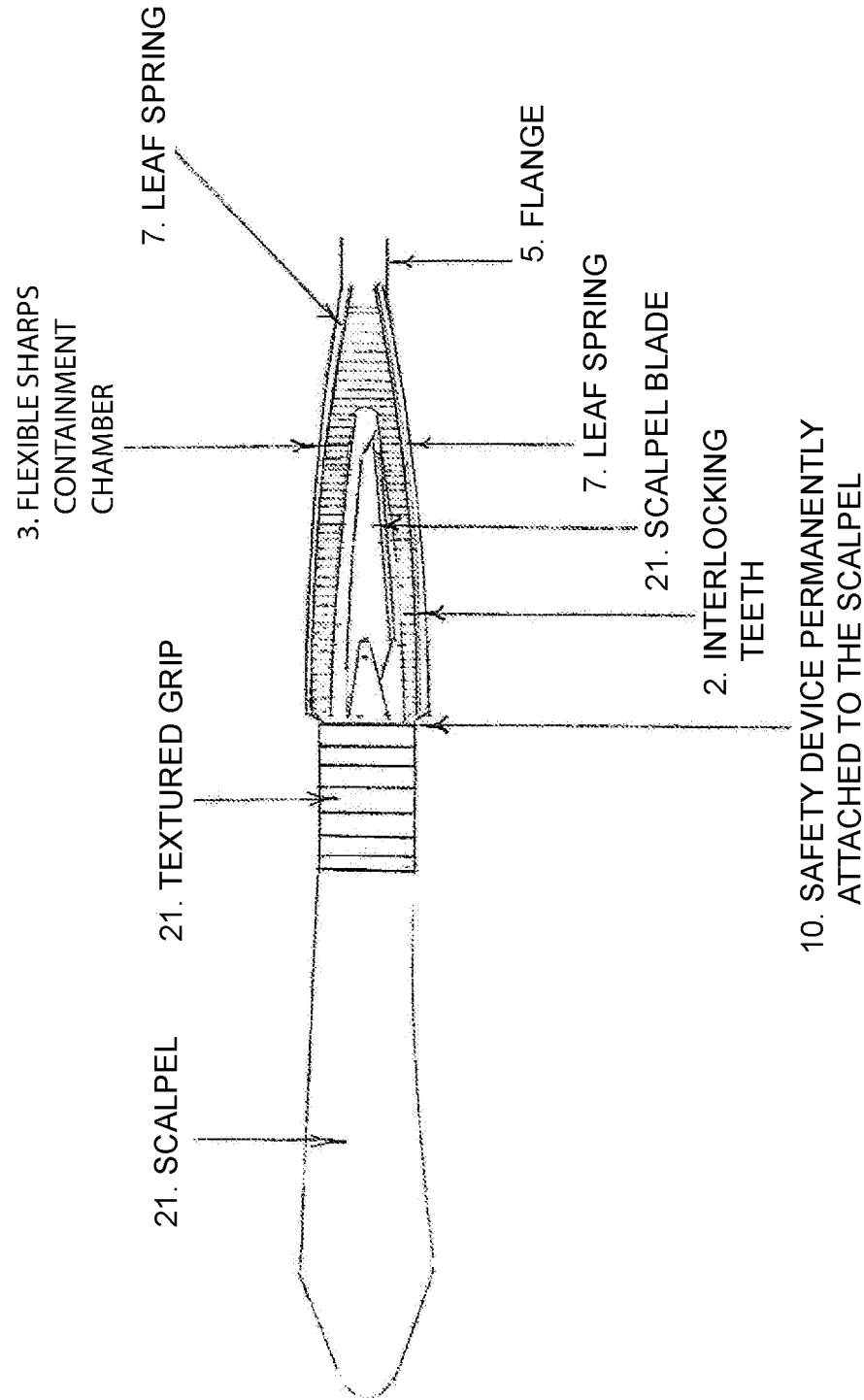
FIG. 13 shows a view of a sharps safety device according to at least one embodiment of the present disclosure.

Explanatory Notes for FIG. 13

Scalpel Internal View with Adaptable Multi-Procedural Sharps Safety Device in the Closed Post-Use Position The notes and discussions on this page refer to the drawing labeled, "FIG. 13". "FIG. 13" is numbered 2, 3, 5, 7, 10 and 21. The numbers are placed throughout the illustration. They are associated with corresponding arrows which point to various sections and aspects of the drawing which need further explanation. This methodology allows for a clear and explanation of the various sections and sub-sections of the mechanism.

Description of FIG. 13

The diagram as shown in "FIG. 13" reveals the "Scalpel Internal View with Adaptable Multi-Procedural Sharps Safety Device in the Closed Post-Use Position". The "Safety Device" in "FIG. 13" (10) is in in the "closed" post-use position. The cutaway view of the device revels the "Scalpel Blade" (21) enclosed within the "Flexible Sharps Containment Chamber" (3). Once the closing process initiates the "Flange" (5) moves forward passing over the "Scalpel Blade" (21) just as it does with the "Injection Needle" "FIG. 1" (6) in order to secure the blade within the "Safety Device [which is] Permanently Attached to the Scalpel" (10). The opening within the "Flange" (5) which allows the "Scalpel Blade" (21) to pass through becomes internally sealed off and the two sides of the "Flexible Sharps Containment Chamber" (3) press together and lock into position preventing the device from being reused and protecting from potential injuries. The "Leaf Springs" (7) likewise move into a "unflexed" position which allows the "Flange" (5) to move forward into position. As is the case with the "Adaptable Multi-Procedural Sharps Safety Device" enclosing a "Injection Needle" "FIG. 1" (6), once "Adaptable Multi-Procedural Sharps Safety Device" "activates" and encloses the "Scalpel Blade" (21) it will never become "inactive". The medical device at this point becomes permanently disabled thus preventing re-use and protecting against potential harm.

Explanation of FIG. 13 Illustration Numbers and their Corresponding Arrows

21. Scalpel
Note: For further information on the "Scalpel" see "Explanatory Notes" for: "FIG. 11" (21).
21. Textured Grip
Note: For further information on the "Textured Grip" see "Explanatory Notes" for: "FIG. 11" (21).
3. Flexible Sharps Containment Chamber
Note: For further information on the "Flexible Sharps Containment Chamber" see "Explanatory Notes" for: "FIG. 11" (3).
See also: For further information on the "Flexible Sharps Containment Chamber" see "Explanatory Notes" for: "FIG. 1" (3).
7. Leaf Spring
Note: For further information on the "Leaf Springs" see "Explanatory Notes" for: "FIG. 11" (7).
See also: For further information on the "Leaf Spring" see "Explanatory Notes" for: "FIG. 1" (7) "FIG. 3" (7).
5. Flange
Note: For further information on the "Flange" see "Explanatory Notes" for: "FIG. 11" (5).
See also: For information on the "Flange" see "Explanatory Notes" for: "FIG. 1" (5), "FIG. 2" (5), and "FIG. 3" (5).
7. Leaf Spring
Note: For further information on the "Leaf Springs" see "Explanatory Notes" for: "FIG. 11" (7).
See also: For further information on the "Leaf Spring" see "Explanatory Notes" for: "FIG. 1" (7) "FIG. 3" (7).
21. Scalpel Blade
Note: For further information on the "Scalpel Blade" see "Explanatory Notes" for: "FIG. 11" (21).
2. Interlocking Teeth Seam
Note: For further information on the "Interlocking Teeth Seam" see "Explanatory Notes" for: "FIG. 12" (2).
See also: For further information on the "Interlocking Teeth" see "Explanatory Notes" for: "FIG. 11" (2).
For further information on the "Interlocking Teeth" see "Explanatory Notes" for: "FIG. 1" (2) and "FIG. 2" (2).
10. Safety Device Permanently Attached to the Scalpel
Note: For further information on the "Safety Device Permanently Attached to the Scalpel" see "Explanatory Notes" for: "FIG. 11" (10).
See also: For further information on the "Safety Device" see "Explanatory Notes" for: "FIG. 12" (10).
For further information on the "Safety Device in the Open Pre-Injection Position" see "Explanatory Notes" for: "FIG. 3" (10), "FIG. 3" "Safety Device Closing Post-Injection" (10), "FIG. 3" "Safety Device Closed" (10).

Figure 14:
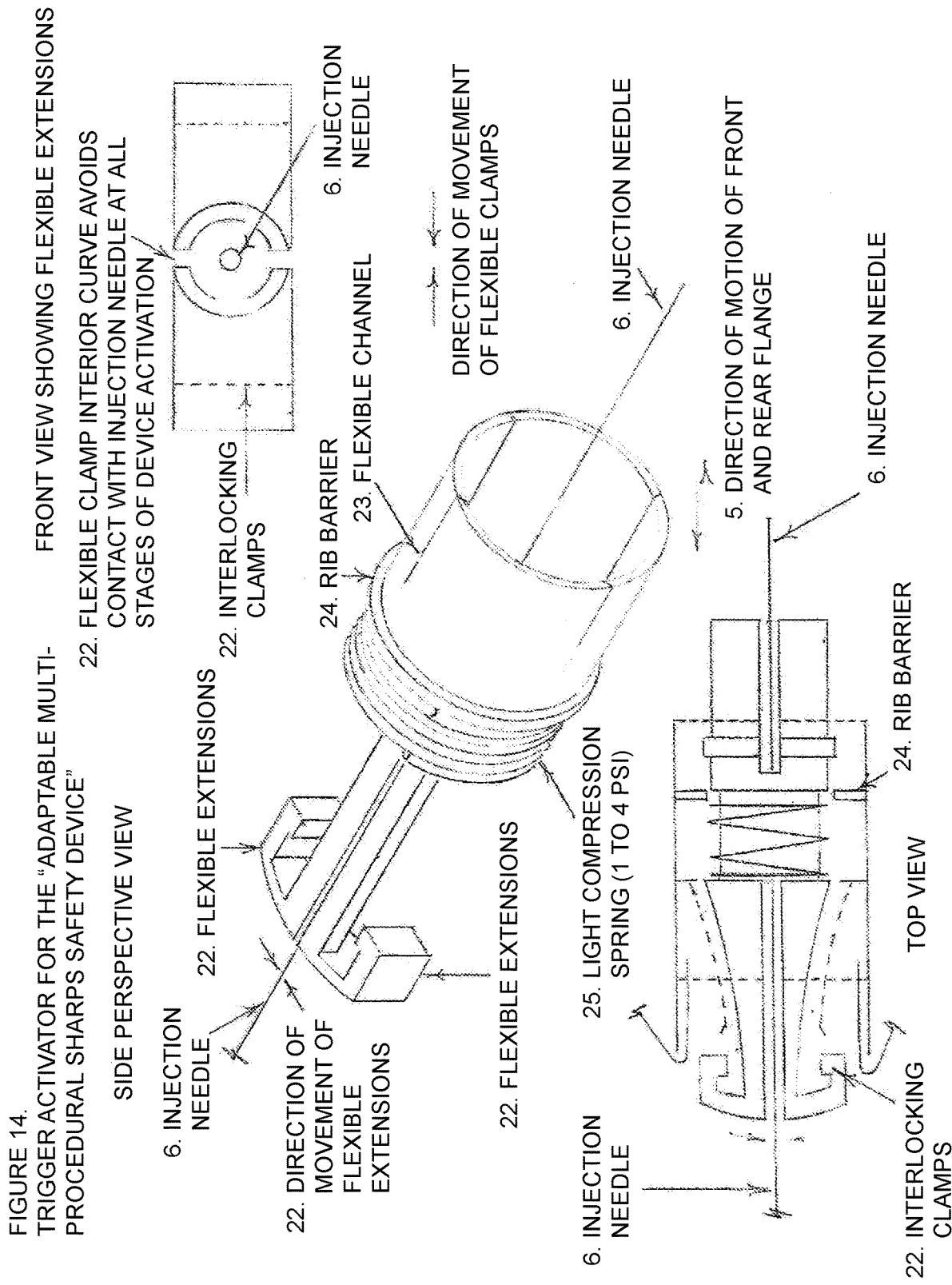
FIG. 14 shows features of a sharps safety device according to at least one embodiment of the present disclosure.
Figure 15:
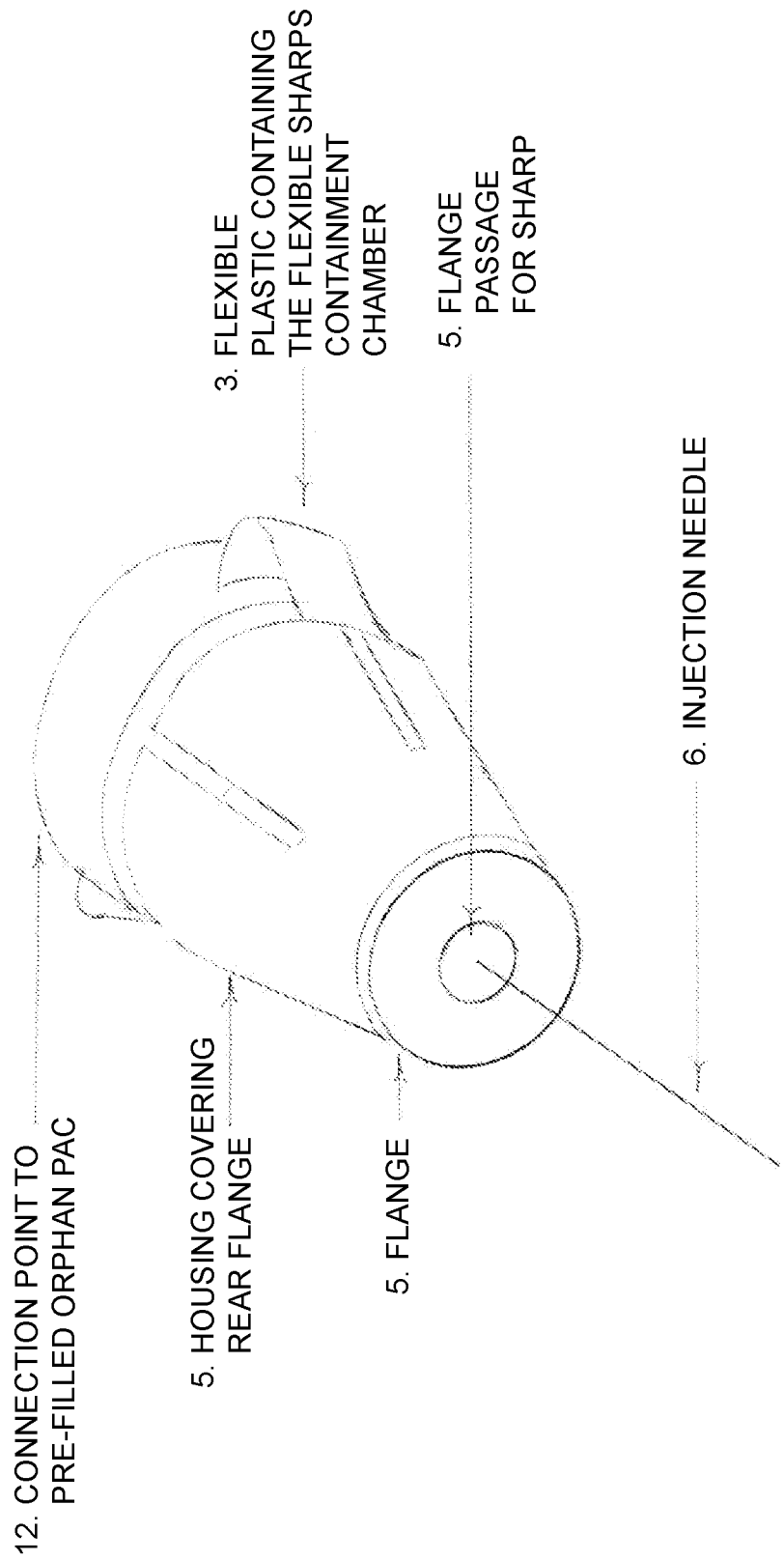
FIG. 15 shows features of a sharps safety device according to at least one embodiment of the present disclosure.

Explanatory Notes for FIG. 14

Trigger Activator for the Adaptable Multi-Procedural Sharps Safety Device

The notes and discussions on this page refer to the drawing labeled, "FIG. 14". "FIG. 14" is numbered 5, 6, 22, 23, 24, and 25. The numbers are placed throughout the illustration. They are associated with corresponding arrows which point to various sections and aspects of the drawing which need further explanation. This methodology allows for a clear and explanation of the various sections and sub-sections of the mechanism.

Description of FIG. 14

The illustration as seen in "FIG. 14" details the "Trigger Activator for the "Adaptable Multi-Procedural Sharps Safety Device". The version of the "Trigger Activator" in the diagram will be used with the "Adaptable Multi-Procedural Sharps Safety Device with optional Orphan Pac", "Adaptable Multi-Procedural Sharps Safety Device" for "Injection Needles" "FIG. 1" (6), as well as the "Scalpel with [the] Adaptable Multi-Procedural Sharps Safety Device" (10). There is however, one minor difference with regard to the "Scalpel with [the] Adaptable Multi-Procedural Sharps Safety Device", that being, the "Adaptable Multi-Procedural Sharps Safety Device" will be manually activated by the surgeon upon completion of the procedure. To activate the "Scalpel with [the] Adaptable Multi-Procedural Sharps Safety Device" a lever or button will be depressed by the user to activate the device. This minor difference is necessary because a surgeon or other medical professional using a scalpel needs the ability to activate the safety device once their medical procedure is fully complete for the patience safety rather than the device activating automatically as is the case with the "Adaptable Multi-Procedural Sharps Safety Device with [the] Orphan Pac" and the "Adaptable Multi-Procedural Sharps Safety Device" with the "Injection Needle" "FIG. 1" (6). In cases where an "Injection Needle" "FIG. 1" (6) is concerned it is vital to have the safety device engage automatically following use in order to protect anyone in the vicinity that may come into contact with the "Injection Needle" "FIG. 1" (6) once it has been used.

As is visible in the diagram in "FIG. 14" the distal end of the "Flexible Extensions" (22) contains the "Interlocking Clamps" (22). These clamps play a vital role in the overall function of the "Adaptable Multi-Procedural Sharps Safety Device". When the safety device is in the "opened" position both sets of flexible clamps remain interlocked with similar stationary clamps at the distal end of the "Rear Flange" (also 5). It is important to note that the "Flexible Extensions" (22) and their "Interlocking Clamps" (22) are attached to the "Front Flange" (5) while the "Interlocking Clamps" (22) which are located at the distal end of the "Rear Flange" (also 5) are attached to the "Rear Flange" (also 5). To avoid contact with the "Injection Needle" (6) at all times the inner cavity of the "Flexible Extensions" (22) are curved. Prevention of contact between the "Injection Needle" (6) and the "Flexible Extensions" (22) as they flex toward each other during all stages of the closure procedure is vital to help prevent potential friction from occurring which could interfere with the function "Adaptable Multi-Procedural Sharps Safety Device." It is also vital to prevent injury from occurring to the individual receiving the injection.

The bottom illustration in "FIG. 14" reveals the "Direction of Motion of Front Flange and Rear Flange" (5). Once the "Front Flange" (5) comes into contact with the individual receiving the injection the "Front Flange" (5) begins to depress inward deeper into the "Rear Flange" (also 5). This process acts as the activator for the "Adaptable Multi-Procedural Sharps Safety Device" to initiate the safety device closure process. As the "Flexible Extensions" (22) which are attached to the distal end of the "Front Flange" (5) travel deeper into the "Rear Flange" (also 5) they pass through a narrow diameter channel located at the distal end of the "Rear Flange" (also 5). This motion causes the "Flexible Extensions" (22) to flex inward toward each other and unlatch the "Interlocking Clamps" (22) located at the end of the "Flexible Extensions" (22) from a similar set of "Interlocking Clamps" (22) located at the distal end of the "Rear Flange" (also 5). The inward retraction of the "Front Flange" (5) into the "Rear Flange" (also 5) continues until the "Light Compression Spring" (25) using a light amount of pressure again reverses the process as it returns to its uncompressed state which results in the withdrawing of the "Front Flange" (5) from the "Rear Flange" (also 5). The "Rib Barrier" (24) which is located at the mid-way point on the exterior of the "Front Flange" (5) abruptly terminates the withdraw motion of the "Front Flange" (5) from the "Rear Flange" (also 5) as it comes into contact with a similar interior "Rib Barrier" (24) located in the anterior position of the "Rear Flange" (also 5). From this point, both the "Front Flange" (5) and the "Rear Flange" (also 5) no longer move independently of each other. Their motion becomes in conjunction with that of the "Adaptable Multi-Procedural Sharps Safety Device" as the safety device moves into a "closed" and "active" position. The "Flexible Extensions" (22) as well as the "Interlocking Clamps" (22) which previously were held perpetually in an interlocked position with their counter parts prior to the initiation of the "closure" procedure do not return to the "open" position as the "Adaptable Multi-Procedural Sharps Safety Device" moves to secure the sharp within the device.

Explanation of FIG. 14 Illustration Numbers and their Corresponding Arrows

6. Injection Needle
   Note: For further information on the "Injection Needle" see "Explanatory Notes" for: "FIG. 1" (6) and "FIG. 5" (6).
22. Flexible Extensions Interior Curve Avoids Contact with Injection Needle at All Stages of Device Activation
   The interior of the "Flexible Extensions" (22) is curved to create a hollow channel within the clamps to prevent contact with the "Injection Needle" "FIG. 1" (6) at any point during the pre and post use process. It is important to prevent contact with the "Injection Needle" "FIG. 1" (6) both to prevent injury to the individual receiving the injection as well as to prevent friction from occurring with the "Injection Needle" "FIG. 1" (6) which may interfere with the safety device closure process. Therefore, at no point will the "Flexible Extension[s]" (22) come into contact with the "Injection Needle" "FIG. 1" (6) including after the "Adaptable Multi-Procedural Sharps Safety Device" has fully "activated".
23. Flexible Channel
   The "Flexible Channel" (23) provides flexibility to the Front Flange (5) by allowing the pieces to function as a joint and "bend" inward without breaking while retracting into the "Rear Flange" (5) thus allowing the "Interlocking Clamps" (22) to unlatch. This step is crucial so that the "Adaptable Multi-Procedural Sharps Safety Device" can instantly activate and move into a "closed" position following an injection to secure the "Injection Needle" "FIG. 1" (6).
6. Injection Needle
   Note: For further information on the "Injection Needle" see "Explanatory Notes" for: "FIG. 1" (6) and "FIG. 5" (6).
5. Direction of Motion of Front Flange and Rear Flange
   The range of motion of the "Front Flange [and] Rear Flange" (5) are depicted in this illustration. The "Front Flange" (5) as has been stated, initially retracts into the "Rear Flange" (also 5) once the safety device closure process has begun which results in the eventual unlatching of the "Interlocking Clamps" (22). At this point the "Front Flange" (5) motion is again reversed due to force being exerted by the "Lite Compression Spring" (25) and the "Front Flange" (5) begins to move forward away from the "Rear Flange" (also 5) until the motion is terminated by the "Rib Barrier" (24). Once this occurs both the "Front Flange [and] Rear Flange[s]" (5) move in unison as the "Adaptable Multi-Procedural Sharps Safety Device" moves into the final "closed" position.
   Note: For information on the "Flange" see "Explanatory Notes" for: "FIG. 1" (5), "FIG. 2" (5), and "FIG. 3" (5).
   See also: For further information on the "Flange" see "Explanatory Notes" for: "FIG. 11" (5).
6. Injection Needle
   Note: For further information on the "Injection Needle" see "Explanatory Notes" for: "FIG. 1" (6) and "FIG. 5" (6).
24. Rib Barrier The "Rib Barrier" (24) as depicted in "FIG. 14" acts as a barrier preventing the "Front Flange" (5) from moving into a reset position once activated. As the "Front Flange" (5) moves in reverse into the "Rear Flange" (also 5) to unlatch the "Interlocking Clamps" (22) it effortlessly travels over the "Rib Barrier" (24) due to its shape and contour. Once the "Front Flange" (5) has traveled into the "Rear Flange" (also 5) and the "Interlocking Clamps" (22) have become detached from each other the "Light Compression Spring" (25) begins pushing the "Front Flange" (5) forward again so that the "Adaptable Multi-Procedural Sharps Safety Device" may move into a "closed" position to secure the "Injection Needle" "FIG. 1" (6). A certain amount of travel forward is permissible to allow alignment of various parts of the safety device during closure however "Front Flange" (5) is restricted once encountering the "Rib Barrier" (24). The "Leaf Springs" "FIG. 1" (7) "FIG. 3" (7) then take over the closure process.

22. Interlocking Clamps

The "Interlocking Clamps" (22) are a vital part of the trigger mechanism of the "Adaptable Multi-Procedural Sharps Safety Device" and are located at the distal end of the "Flexible Extensions" (22). They interlock with matching clamps at the distal end of the "Rear Flange" (also 5). Prior to the "Adaptable Multi-Procedural Sharps Safety Device" becoming "active" both sets of clamps are firmly interlocked together preventing the safety device from prematurely activating and beginning the closure procedure.

6. Injection Needle

Note: For further information on the "Injection Needle" see "Explanatory Notes" for: "FIG. 1" (6) and "FIG. 5" (6).

25. Light Compression Spring 1 to 4 PSI

The "Light Compression Spring" (25) is a vital portion of the "Trigger Activator" assembly because it is what causes the retraction of the "Front Flange" (5) from the "Rear Flange" (also 5) once the "Interlocking Clamps" (22) become detached from each other. As the "Front Flange" (5) moves deeper into the "Rear Flange" (also 5) the "Light Compression Spring" (25) becomes stretched and elongated until the "Front Flange" (5) can travel no further into the "Rear Flange" (also 5). The two "Flexible Extensions" (22) become compressed at nearly 90°. It is at this point that the "Light Compression Spring" (25) starts to return to its natural retracted state utilizing perhaps 1 to 4 PSI of force pulling the "Front Flange" (5) out of the "Rear Flange" (also 5) until coming into contact with the "Rib Barrier" (24) which brings the motion of the "Front Flange" (5) to a halt. Now, the "Leaf Springs" "FIG. 1" (7) continue the process until the "Adaptable Multi-Procedural Sharps Safety Device" securely "closed".

22. Direction of Motion of Flexible Extensions

The "Flexible Extensions" (22) remain in a stationary and "open" position when the "Front Flange" (5) and the "Rear Flange" (also 5) are held in place by the "Interlocking Clamps" (22) within the "Adaptable Multi-Procedural Sharps Safety Device". However, once the "Front Flange" (5) is activated and begins to retract into the "Rear Flange" (also 5) during the closure procedure the "Interlocking Clamps" (22) become detached from each other. As the "Front Flange" (5) retracts deeper into the "Rear Flange" (also 5) the narrow-concaved diameter of the distal opening of the "Rear Flange" (also 5) begins to compress the two "Flexible Extensions" (22) together moving them into a nearly 90° position inward. Therefore, the range of motion of the "Flexible Extensions" (22) is inwardly allowing the "Front Flange" (5) and "Rear Flange" (also 5) to become detached from each other. Then, as the "Front Flange" (5) again reverses its direction of movement and begins to pull away from the "Rear Flange" (also 5) due to interior pressure applied by the "Light Compression Spring" (25) the "Adaptable Multi-Procedural Sharps Safety Device" moves forward toward the "closed" position.

22. Flexible Extensions

The "Flexible Extensions" (22) are pliable legs extending from the body of the "Front Flange" (5). Attached to the distal end of the "Flexible Extensions" (22) and opposite the "Front Flange" (5) are the "Flexible Extensions" (22). These are a key component of the activator mechanism within "Adaptable Multi-Procedural Sharps Safety Device" which maintains the safety device in the "open" position prior to activation. Once the "Front Flange" (5) makes contact with the individual receiving the injection it begins to retract inward within the "Rear Flange" (also 5). As the "Flexible Extensions" (22) pass through the narrowing diameter at the distal end of the "Rear Flange" (also 5) the "Flexible Extensions" (22) begin flexing inward detaching the "Interlocking Clamps" (22) from the "Rear Flange" (also 5). At this point, the "Front Flange" (5) is no longer attached to the "Rear Flange" (also 5) and the "Adaptable Multi-Procedural Sharps Safety Device" activation procedure is able to begin.

Note: For further information on the "Direction of Motion of Flexible Extensions" see "Explanatory Notes" for: "FIG. 14" (22).

6. Injection Needle

Note: For further information on the "Injection Needle" see "Explanatory Notes" for: "FIG. 1" (6) and "FIG. 5" (6).

22. Flexible Extensions

Note: For further information on the "Flexible Extensions" see "Explanatory Notes" for: "FIG. 14" (22).

For further information on the "Direction of Motion of Flexible Extensions" see "Explanatory Notes" for: "FIG. 14" (22).

24. Rib Barrier

Note: For information on the "Rib Barrier" see "Explanatory Notes" for: "FIG. 14" (24).

22. Interlocking Clamps

Note: For further information on the "Interlocking Clamps" see "Explanatory Notes" for: "FIG. 14" (22).

Additional Information for the Adaptable Multi-Procedural Sharps Safety Device

17. Breakable Seal on the Pre-Filled Orphan Pac

As the individual performing the injection threads the "Adaptable Multi-Procedural Sharps Safety Device" "FIG. 9" (17), "FIG. 3" "Safety Device Closing Post-Injection" (10), "FIG. 3" "Safety Device Closed" (10) onto their selected "Pre-filled Orphan Pac" "FIG. 7" (17) a safety seal on the "Pre-filled Orphan Pac" is penetrated thus allowing the medication contents stored within the "Pre-filled Medication Fluid Pac" "FIG. 7" (18) to flow freely toward the patient when direct pressure is applied by the fingers to the "Medication Fluid Pac" "FIG. 7" (18).

19. Valve on the Internal Portion of the "External Injection Port" on "Pre-Filled Orphan Pac" Prevents Medications from Leaking Out Within the "Pre-filled Orphan Pac" at the internal entrance of the "External Injection Port" is a valve that only opens inward into the "Pre-filled Orphan Pac." "FIG. 7" (13) When additional medications are injected by a medical professional into the "External Injection Port" the medication flows directly into the "Pre-filled Orphan Pac" "FIG. 7" (17). The internal valve contained at the entrance of the "External Injection Port" prevents medications from flowing backward toward the "External Injection Port" from the "Pre-filled Orphan Pac."

19. Length of the External Injection Port is Long Enough for Safe Adding of Additional Medication

There are instances in which a medical professional may determine that there is a need to add additional medication to that already contained within the "Pre-filled Orphan Pac" prior to performing an injection on a patient. The "External Injection Port" exist for this purpose. It allows the professional to do so safely without risking damage or contamination to either the "Adaptable Multi-Procedural Sharps Safety Device" "FIG. 3" (10) or "Pre-filled Orphan Pac" (17), or injury to themselves. The "External Injection Port" will be of sufficient length extending away from the rear portion of the "Pre-filled Orphan Pac" to allow the medical professional to safely hold and add additional medications to the "Pre-filled Orphan Pac" "FIG. 7" (17). Small finger grip extensions will protrude on either side of the tip of the "External Injection Port" tubing to allow the tubing to be held and slightly elevated enough by the medical professional so that additional medication can be added to the "External Injection Port" utilizing a syringe. When the "External Injection Port" is not in use it remains safely adhered to the exterior of the "Pre-filled Orphan Pac."

17. Pressure on and within the Pre-Filled Orphan Pac Moves the Medication Forward

As slight pressure is applied by the fingers to the exterior of the "Pre-filled Medication Fluid Pac" "FIG. 7" (18) during the injection process the fluid medication contained within the "Medication Fluid Pac" moves forward toward the patient. Once pressure has been applied by the individual performing the injection, the "Pre-filled Medication Fluid Pac" "FIG. 7" (18) continues to concave inward on its own at a steady rate. This is due to the release of internal pressure contained within the "Pre-filled Medication Fluid Pac" as the medication flows forward toward and into the patient during the injection. This process allows all medication contained within the "Medication Fluid Pac" to be dispersed evenly into the patient leaving no residual medication behind. Once the "Pre-filled Medication Fluid Pac" "FIG. 7" (18) is completely compressed the medication delivery process is complete.

While this disclosure has been described as having preferred designs, the apparatus, and methods according to the present disclosure can be further modified within the scope and spirit of this disclosure. This application is therefore intended to cover any variations, uses, or adaptations of the disclosure using its general principles. For example, any method disclosed herein and in the appended claims represent one possible sequence of performing the steps thereof. A practitioner may determine in a particular implementation that a plurality of steps of one or more of the disclosed methods may be combinable, or that a different sequence of steps may be employed to accomplish the same results. Each such implementation falls within the scope of the present disclosure as disclosed herein and in the appended claims. Furthermore, this application is intended to cover such departures from the present disclosure as come within known or customary practice in the art to which this disclosure pertains.

What is claimed is:

1. A medical sharp safety device, the medical sharp safety device comprising:
   - a reservoir connector configured for attachment to a medicament-containing reservoir;
   - a sharp containment flange, said sharp containment flange comprising a proximal end and a distal end and a passageway through said sharp containment flange from said proximal end through said distal end;
   - at least two opposing flexible plastic strips each connected at a first end to said reservoir connector and at a second end to said sharp containment flange, each of said at least two opposing flexible plastic strips each comprising an embedded leaf spring, each of said at least two opposing flexible plastic strips comprising a medical sharp facing inner surface and an opposing outer surface, each said medical sharp facing inner surface comprising projections therefrom on a majority of each said medical sharp facing inner surface, wherein said projections on a first said flexible plastic strip are configured to interlock with said projections on a second said flexible plastic strip when said medical sharp facing inner surface of said first flexible plastic strip comes into contact with said medical sharp facing inner surface of said second flexible plastic strip;
   - wherein when said reservoir connector is attached to said medicament-containing reservoir and a medical sharp is inserted through said passageway, said leaf springs of at least two opposing flexible plastic strips are placed into a spring-biased state and said medical sharp appears from said distal end of said sharp containment flange.

2. The medical sharp safety device of claim 1, wherein said reservoir connector is configured as a Luer fitting.

3. The medical sharp safety device of claim 1, wherein when said at least two opposing flexible plastic strips interlock, said medical sharp is inaccessible.

4. The medical sharp safety device of claim 1, wherein when said at least two opposing flexible plastic strips interlock, any medicament residue or biological fluids on or in said medical sharp are sealed within said sharp containment flange and said flexible plastic strips.

5. The medical sharp safety device of claim 1, wherein said medicament-containing reservoir is an orphan pac.

6. The medical sharp safety device of claim 5, wherein said orphan pac is a single-use orphan pac irremovably attached to said reservoir connector.

7. The medical sharp safety device of claim 1, wherein said leaf springs comprise a shape memory material.

8. The medical sharp safety device of claim 1, wherein said reservoir connector comprises a ball joint, said ball joint being rotatable whereby the orientation between said medical sharp and said medicament-containing reservoir may be adjusted.

9. The medical sharp safety device of claim 8, wherein said ball joint may be locked so that the orientation of said medical sharp and said medicament-containing reservoir is fixed.

10. The medical sharp safety device of claim 1, further comprising flexible extensions inside said sharp containment flange.

11. The medical sharp safety device of claim 10, wherein said flexible extensions comprise a curvature allowing said medical sharp to pass between said flexible extensions without contacting said flexible extensions.

12. The medical sharp safety device of claim 1, wherein when said at least two opposing flexible plastic strips are released from said spring-biased state, said projections on said at least two opposing flexible plastic strips interlock so that said at least two opposing flexible plastic strips and said sharp containment flange together permanently envelop said medical sharp that was within said passageway so that any medicament residue and/or biological fluids on or in said medical sharp are sealed within said flexible plastic strips and said sharp containment flange.

13. A medical sharp safety device, the medical sharp safety device comprising:
- a reservoir connector configured for attachment to a medicament-containing reservoir,
- a sharp containment flange, said sharp containment flange comprising a proximal end and a distal end and a passageway through said sharp containment flange from said proximal end through said distal end;
- at least two opposing flexible plastic strips each connected at a first end to said reservoir connector and at a second end to said sharp containment flange, each of said at least two opposing flexible plastic strips each comprising an embedded leaf spring, each of said at least two opposing flexible plastic strips comprising a medical sharp facing inner surface and an opposing outer surface, each said medical sharp facing inner surface comprising projections therefrom on a majority of each said medical sharp facing inner surface, wherein said projections on a first said flexible plastic strip are configured to interlock with said projections on a second said flexible plastic strip when said medical sharp facing inner surface of said first flexible plastic strip comes into contact with said medical sharp facing inner surface of said second flexible plastic strip, and wherein said projections on said at least two opposing flexible plastic strips are interlocked so that said at least two opposing flexible plastic strips and said sharp containment flange together permanently envelop a medical sharp so that any medicament residue and/or biological fluids on or in said medical sharp are sealed within said flexible plastic strips and said sharp containment flange.

14. The medical sharp safety device of claim 13, wherein said reservoir connector is configured as a Luer fitting.

15. The medical sharp safety device of claim 13, wherein said medicament-containing reservoir is an orphan pac.

16. The medical sharp safety device of claim 15, wherein said orphan pac is a single-use orphan pac irremovably attached to said reservoir connector.

17. The medical sharp safety device of claim 13, wherein said leaf springs comprise a shape memory material.

18. The medical sharp safety device of claim 13, wherein said reservoir connector comprises a ball joint, said ball joint being rotatable whereby the orientation between said medical sharp and said medicament-containing reservoir may be adjusted.

19. The medical sharp safety device of claim 18, wherein said ball joint may be locked so that the orientation of said medical sharp and said medicament-containing reservoir is fixed.

\* \* \* \* \*